US008628931B2

(12) United States Patent
Liotta et al.

(10) Patent No.: US 8,628,931 B2
(45) Date of Patent: Jan. 14, 2014

(54) MTOR PATHWAY THERANOSTIC

(75) Inventors: Lance A. Liotta, Rockville, MD (US); Emanuel F. Petricoin, III, Rockville, MD (US); Virginia Espina, Rockville, MD (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1276 days.

(21) Appl. No.: 12/083,866

(22) PCT Filed: Oct. 18, 2006

(86) PCT No.: PCT/US2006/040708
§ 371 (c)(1),
(2), (4) Date: Jan. 16, 2009

(87) PCT Pub. No.: WO2007/047754
PCT Pub. Date: Apr. 26, 2007

(65) Prior Publication Data
US 2009/0148859 A1    Jun. 11, 2009

Related U.S. Application Data

(60) Provisional application No. 60/727,510, filed on Oct. 18, 2005.

(51) Int. Cl.
*G01N 33/53* (2006.01)
*G01N 33/50* (2006.01)
*G01N 33/52* (2006.01)

(52) U.S. Cl.
USPC ........... 435/7.23; 435/7.1; 435/7.2; 435/7.21; 435/40.51; 435/40.52; 435/967; 435/973; 436/501; 436/503; 436/63; 436/64

(58) Field of Classification Search
USPC ........... 435/7.1, 7.2, 7.21, 7.23, 40.51, 40.52, 435/967, 973; 436/501, 503, 63, 64
See application file for complete search history.

(56) References Cited

U.S. PATENT DOCUMENTS

| 2002/0015974 A1 | 2/2002 | Bacus et al. |
| 2003/0153014 A1 | 8/2003 | Shen et al. |
| 2005/0131006 A1 | 6/2005 | Mukherjee et al. |
| 2008/0108091 A1 | 5/2008 | Hennessy et al. |

FOREIGN PATENT DOCUMENTS

| EP | 1 491 894 A | 12/2004 |
| WO | WO 01/27624 A | 4/2001 |
| WO | WO 01/79855 A | 10/2001 |
| WO | WO 2004/089294 A | 10/2004 |
| WO | WO 2005/037071 A | 4/2005 |
| WO | WO 2005/064343 A | 7/2005 |
| WO | WO 2005/097107 A2 | 10/2005 |

OTHER PUBLICATIONS

Nathan, C.-A. O., et al. Clinical Cancer Research, 10: 5820-5827, Sep. 1, 2004.*
Zhou, X., et al., Clinical Cancer Research, 10: 6779-6788, Oct. 15, 2004.*
Belluco, C., et al. Clinica Chimica Acta, 357: 180-183, 2005.*
Wang, Y., et al., Journal of Neuroscience Research, 85: 2360-2373, 2007.*
Cowherd Stacy M et al: "Proteomic analysis of human breast cancer tissue with laser-capture microdissection and reverse-phase protein microarrays." Clinical Breast Cancer vol. 5, No. 5, Dec. 2004 pp. 385-392.
Gulmann Christian et al: Proteomic analysis of apoptotic pathways reveals prognostic factors in follicular lymphoma.: Clinical Cancer Research: an Official Journal of the American Association for Cancer Research Aug. 15, 2005, vol. 11, No. 16, pp. 5847-5855.
Petricoin Emanuel F III et al: Mapping molecular networks using proteomics: a vision for patient-tailored combination therapy.: Journal of Clinical Oncology: Official Journal of the American Society of Clinical Oncology May 20, 2005, vol. 23, No. 15 pp. 3614-3621.
Wulfkuhle J et al.: "Genomic and proteomic technologies for individualisation and improvement of cancer treatment" European Journal of Cancer, Pergamon Press, Oxford, GB, vol. 40, No. 17, Nov. 2004, pp. 2623-2632.
Wulfkuhle Julia D et al. Signal pathway profiling of ovarian cancer from human tissue specimens using reverse-phase protein microarrays. PROTEOMICS Nov. 2003, vol. 3. No. 11, Nov. 2003, pp. 2085-2090.
Espina Virginia et al: "Pathology of the future: molecular profiling for targeted therapy." Cancer Investigation 2005, vol. 23, No. 1, 2005, pp. 36-46.
International Search Report issued in Application No. PCT/US2006/040708, dated Apr. 5, 2007.
International Preliminary Report on Patentability of the International Bureau of WIPO on International App. No. PCT/US/2006/040708 for mTor Pathway Theranostic, Apr. 23, 2008.

* cited by examiner

*Primary Examiner* — Misook Yu
*Assistant Examiner* — Anne Holleran
(74) *Attorney, Agent, or Firm* — Geoffrey M. Karny

(57) ABSTRACT

This invention relates, e.g., to a method for predicting a subject's response to a chemotherapeutic agent and/or the subject's prognosis, comprising measuring the phosphorylation state of at least one member of the mTOR pathway, and/or of at least one member of an interconnected polypeptide pathway (e.g. a member of the Akt pathway or a member of the IRS pathway), compared to a baseline value, in a cancer tissue or cancer cell sample from the subject, wherein an elevated level of the phosphorylation state compared to the baseline value indicates that the subject is a non-responder to the chemotherapeutic agent and/or has a poor prognosis. Also described is a method for treating a cancer in a subject in need thereof, wherein the subject exhibits an elevated level of the phosphorylation state, comprising administering one or more inhibitors of the mTOR and/or an interconnected pathway.

28 Claims, 18 Drawing Sheets

A

|  | Table 1a<br>Set 1 (n = 33) | | Table 1b<br>Set 2 (n = 26) | |
| --- | --- | --- | --- | --- |
| Characteristic | Patients | Percentage | Patients | Percentage |
| Age (years) | | | | |
| <1 | 1 | 3.0 | 0 | 0 |
| 1-9 | 23 | 69.7 | 19 | 73.1 |
| 10+ | 9 | 27.3 | 7 | 26.9 |
| Gender | | | | |
| Male | 23 | 69.7 | 19 | 73.1 |
| Female | 10 | 30.3 | 7 | 26.9 |
| Site | | | | |
| Extremity | 6 | 18.2 | 5 | 19.2 |
| Genitourinary - Bladder/Prostate | 5 | 15.1 | 7 | 26.9 |
| Head and Neck | 12 | 36.4 | 10 | 38.5 |
| Orbit | 1 | 3.0 | 1 | 3.8 |
| Other | 9 | 27.3 | 3 | 11.5 |
| Histology | | | | |
| Alveolar | 20^ | 60.6 | 7 | 26.9 |
| Embryonal | 11 | 33.3 | 19 | 73.1 |
| Botyroid | 2 | 6.1 | 0 | 0 |
| Tumor Treatment# | | | | |
| VAC | 15 | 45.5 | 9 | 34.6 |
| VAI | 6 | 18.2 | 6 | 23.1 |
| VCT | 4 | 12.1 | 0 | 0 |
| VIE | 8 | 24.2 | 7 | 26.9 |
| nrVAC | 0 | 0 | 4 | 15.4 |

^ Mixed alveolar/embryonal/spindle cell cases classified as alveolar (n = 4 mixed histological subtypes).
Treatment: VAC - Vincristine, Actinomycin-D, Cyclophosphamide; VAI - Vincristine, Actinomycin-D, Ifosfamide; VCT - Vincristine, Cyclophosphamide, Topotecan; VIE - Vincristine, Ifosfamide, Etoposide; nrVAC - No radiation Vincristine, Actinomycin-D, Cyclophosphamide.

FIG. 1A

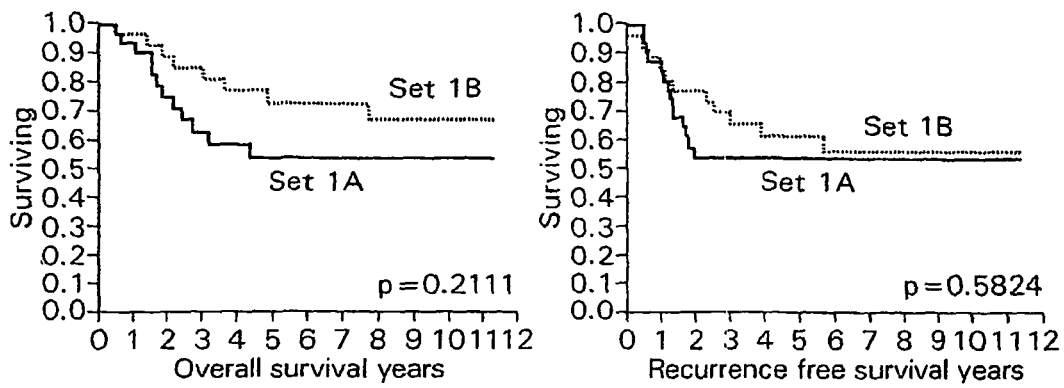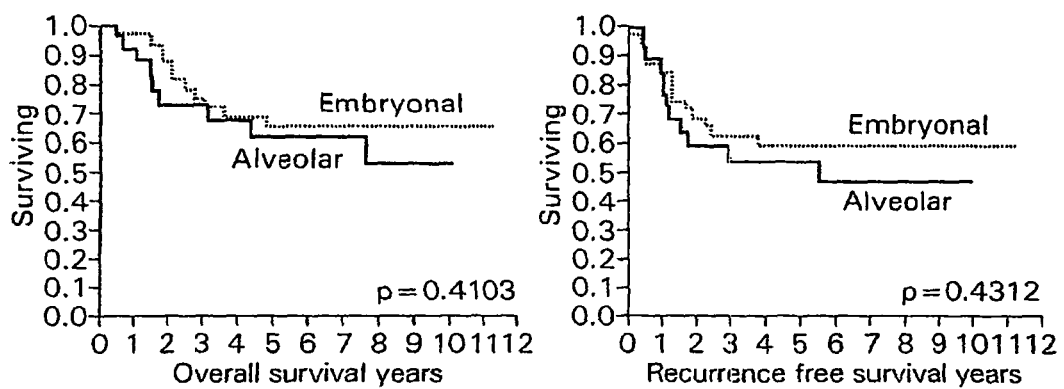
FIG. 1B-C

B

|  | Cluster 1 (Percent) n = 13 | Cluster 2 (Percent) n = 15 | Fisher's Exact Test |
|---|---|---|---|
| Age | | | |
| <9 years | 92% | 67% | p = 0.17 |
| 10+ | 8% | 33% | |
| Sex | | | |
| Male | 85% | 60% | p = 0.22 |
| Female | 15% | 40% | |
| Primary Site | | | |
| Parameningeal H&N | 62% | 27% | p = 0.06 |
| non-PM | 38% | 73% | |
| Histology | | | |
| Embryonal | 62% | 27% | p = 0.06 |
| Alveolar | 38% | 73% | |
| Tumor Invasion | | | |
| T-1 | 8% | 3% | p = 0.17 |
| T-2 | 92% | 67% | |
| Nodal Status-stage | | | |
| N-0 | 69% | 87% | p = 0.37 |
| N-1 | 31% | 13% | |

FIG. 2B

A
Comparison of Protein Array Endpoint Means for RMS
Tumors from Survivors and Non-survivors
n = 33*, df = 1
| Protein | Chi Square | Probablility > Chi Square |
|---|---|---|
| 4EBP1 *(n = 32) | 7.4242 | 0.0064 |
| BCL-2 | 0.8374 | 0.3601 |
| FKHR ser256 | 0.0504 | 0.8223 |
| eIF4E | 0.0126 | 0.9106 |
| eIF4E ser209 | 0.0505 | 0.8223 |
| eIF4G ser1108 | 1.779 | 0.2778 |
| IRS-1 ser612 | 1.7157 | 0.1902 |
| GSK3 β | 2.5896 | 0.1076 |
| GSK2 αβ Y279/216 | 0.6176 | 0.4319 |
| P70S6 | 2.0224 | 0.1550 |
| HIF1-alpha | 2.5896 | 0.1076 |
| AKT | 0.8754 | 0.3495 |
| AKT ser473 | 1.3459 | 0.2460 |
| 4EBP1 ser65 | 2.2926 | 0.1300 |
| 4EBP1 Thr37/46 | 6.1008 | 0.0135 |
B
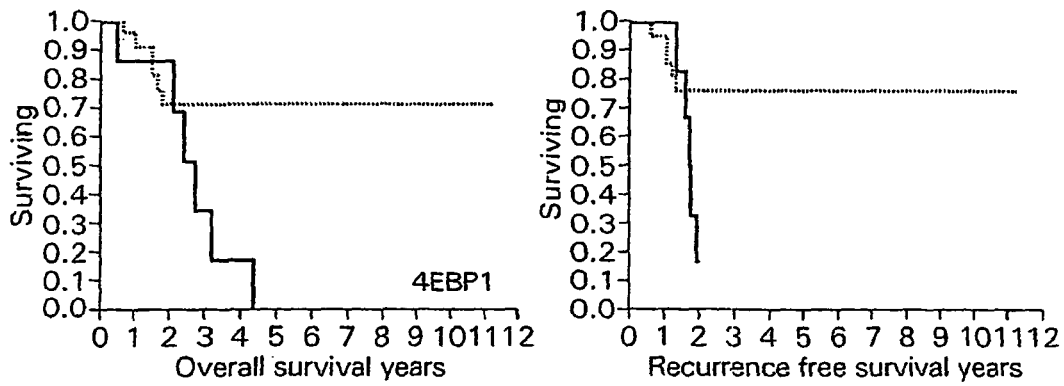
FIG. 3A-B A
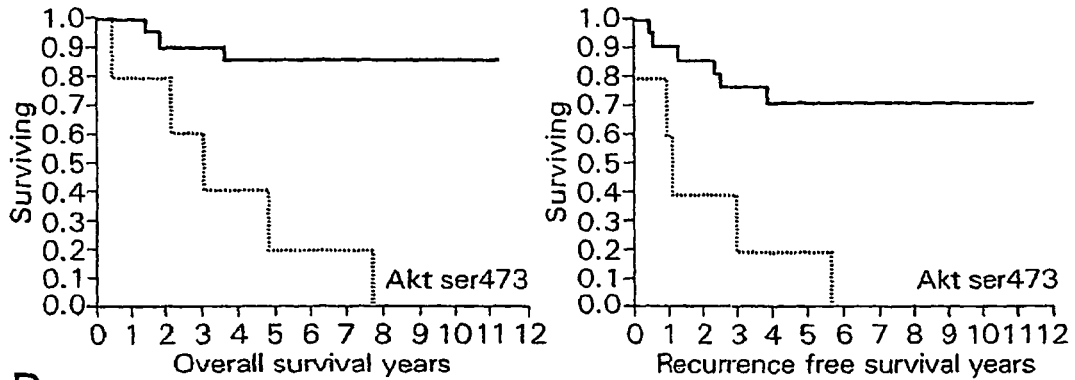
B
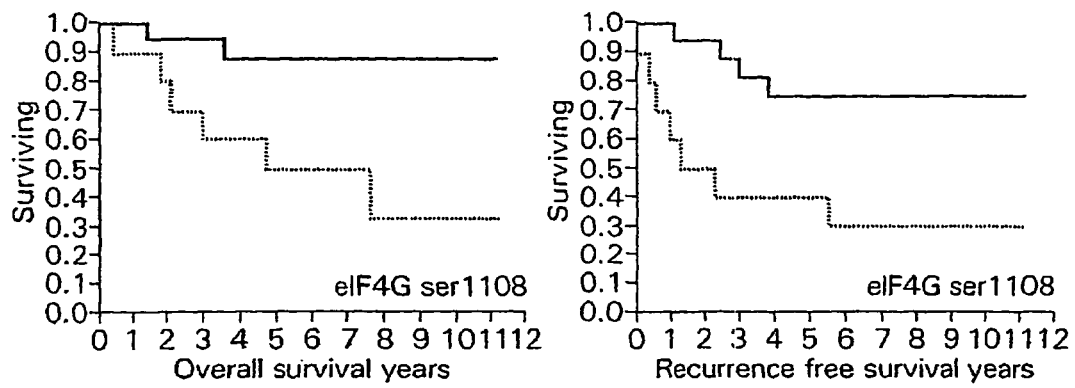
C
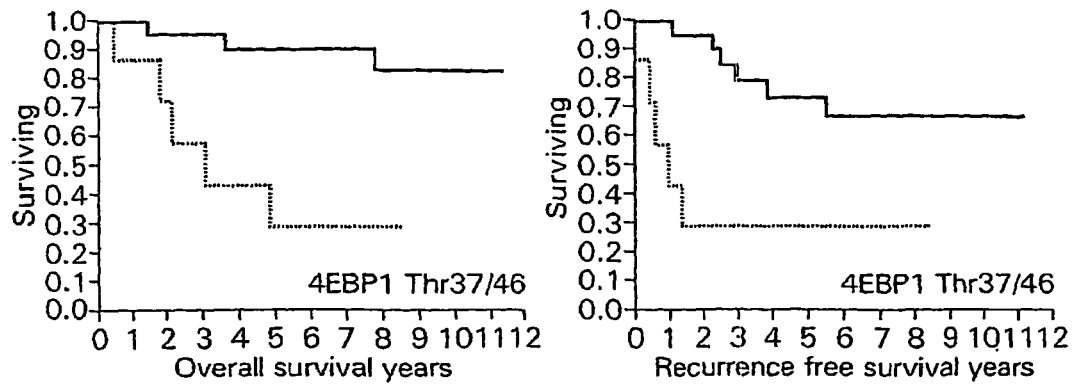
FIG. 4A-C

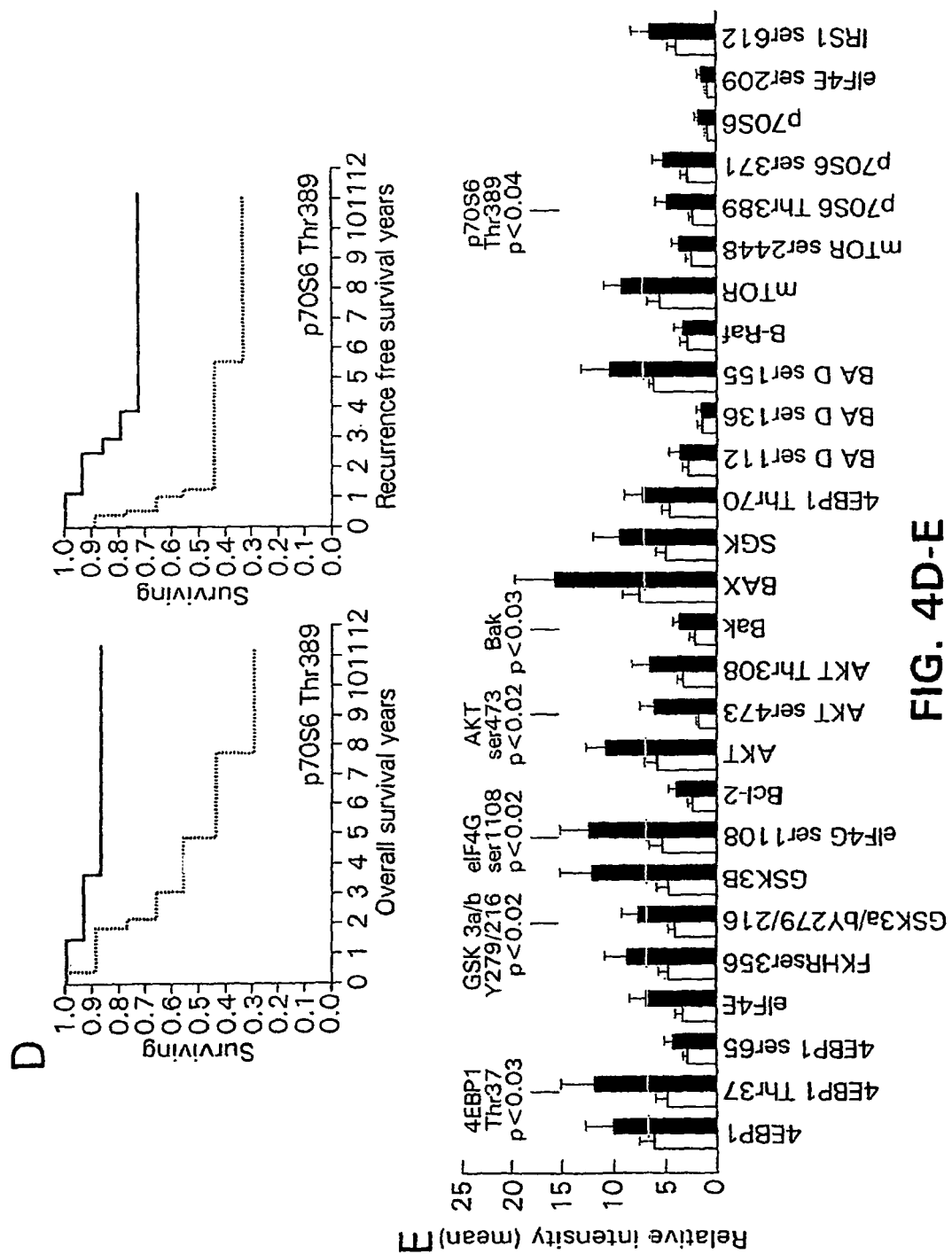
FIG. 4D-E

A

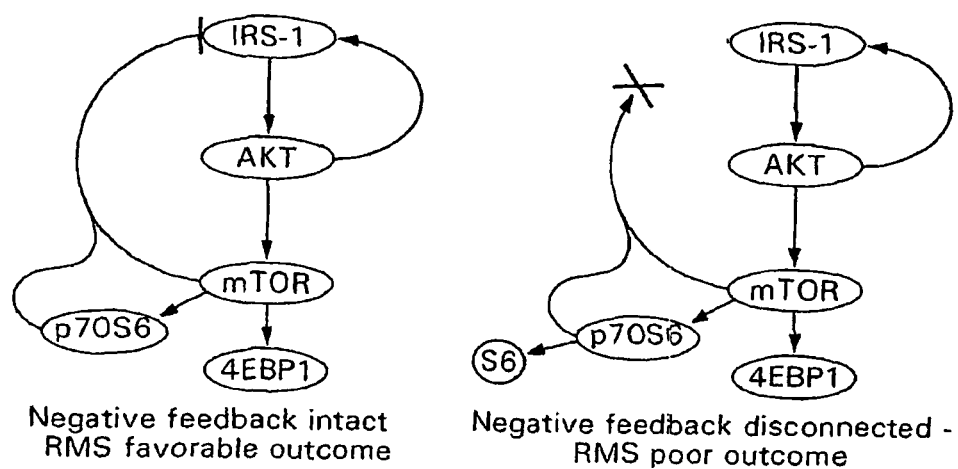

Negative feedback intact
RMS favorable outcome

Negative feedback disconnected -
RMS poor outcome

B

| Variable | by Variable | Survivor Prob>IRhoI | Non-Survivor Prob>IRhoI |
|---|---|---|---|
| IRS-1 ser612 | AKT Thr308 | 0.00153 | 0.10173 |
| IRS-1 ser612 | SGK | 0.00022 | 0.00385 |
| IRS-1 ser612 | GSK3a/bY279/216 | 0.00012 | 0.26040 |
| IRS-1 ser612 | FKHR ser256 | 0.00002 | 0.00653 |
| IRS-1 ser612 | B-Raf | 0.00002 | 0.18272 |
| IRS-1 ser612 | mTOR | 0.00012 | 0.01490 |
| IRS-1 ser612 | mTOR ser2448 | 0.00269 | 0.73576 |
| IRS-1 ser612 | eIF4E | 0.00401 | 0.28940 |
| IRS-1 ser612 | 4EBP1 ser65 | 0.00002 | 0.13896 |
| IRS-1 ser612 | 4EBP1 Thr70 | 0.00003 | 0.03655 |
| IRS-1 ser612 | eIF4E ser209 | 0.00057 | 0.10173 |
| IRS-1 ser612 | eIF4G ser1108 | 0.00002 | 0.20703 |
| IRS-1 ser612 | p70 S6 Thr389 | 0.00004 | 0.18272 |
| IRS-1 ser612 | p70 S6 ser371 | 0.00008 | 0.20703 |
| IRS-1 ser612 | BADser112 | 0.00095 | 0.57016 |
| IRS-1 ser612 | BADser136 | $1.67 \times 10^{-9}$ | 0.45564 |
| IRS-1 ser612 | BADser155 | 0.00011 | 0.11953 |
| IRS-1 ser612 | Bak | 0.00011 | 0.05799 |
| IRS-1 ser612 | BAX | $1.67 \times 10^{-9}$ | 0.00385 |
| IRS-1 ser612 | Bcl-2 | 0.00040 | 0.11953 |

FIG. 5A-B

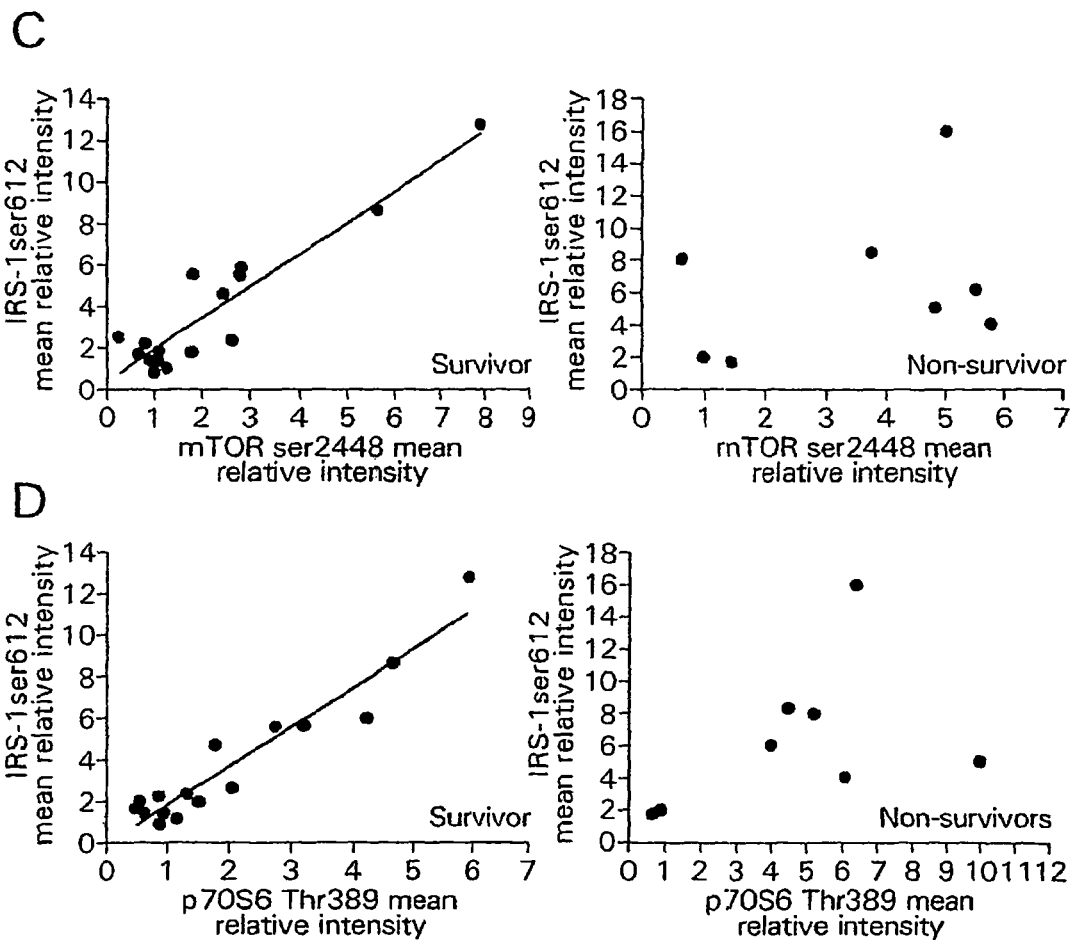
FIG. 5C-D

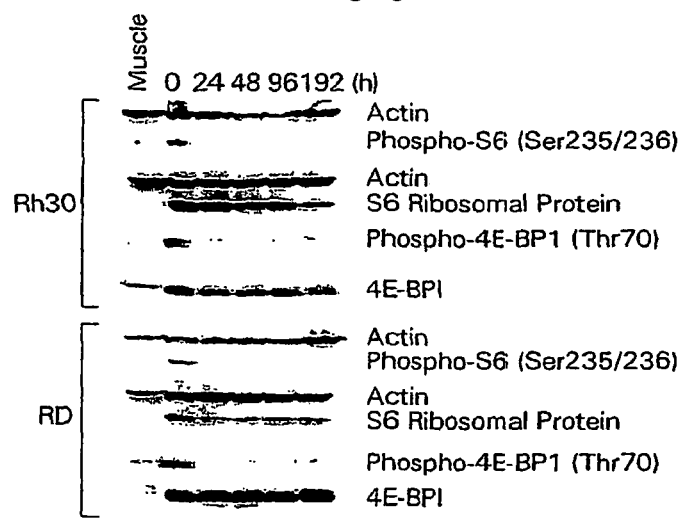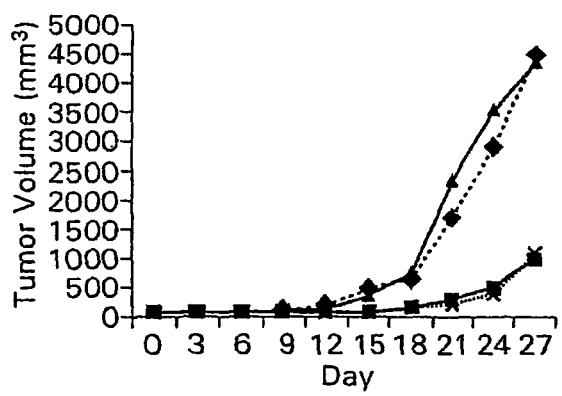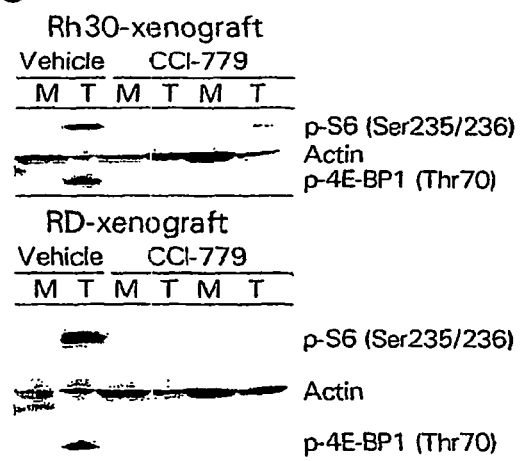
FIG. 6

Time to event: survival months NDI
Censored by censor
Grouped by category

Summary

| Group | N Failed | N Censored | Mean | Std Error |
|---|---|---|---|---|
| Long | 8 | 2 | 84.7217 | 7.71173 |
| Short | 5 | 5 | 15.7358 Biased | 2.07913 |
| Combined | 13 | 7 | 64.8509 | 9.63868 |

Quantiles

| Group | Median Time | Lower 95% | Upper 95% | 25% Failures | 75% Failures |
|---|---|---|---|---|---|
| Long | 80.2 | 60.133 | 98.4 | 69.033 | 98.4 |
| Short | 20 | 2.9667 | - | 13.533 | - |
| Combined | 69.033 | 30 | 95.633 | 20 | 95.633 |

Tests Between Groups

| Test | Chi Square | DF | Prob > Chi Square |
|---|---|---|---|
| Long-Rank | 8.7975 | 1 | 0.0030 |
| Wilcoxon | 7.5758 | 1 | 0.0059 |

Time to event: survival months NDI
Censored by censor
Grouped by pAKT ser473 cutpoint Summary

| Group | N Failed | N Censored | Mean | Std Error |
|---|---|---|---|---|
| High | 4 | 4 | 16.2958 Biased | 2.04952 |
| Low | 9 | 3 | 58.2806 | 14.7889 |
| Combined | 13 | 7 | 61.8645 | 12.2411 |

Quantiles

| Group | Median Time | Lower 95% | Upper 95% | 25% Failures | 75% Failures |
|---|---|---|---|---|---|
| High | - | 7.6333 | - | 13.533 | - |
| Low | 60.6 | 15.067 | - | 15.9 | 95.633 |
| Combined | 60.6 | 15.067 | - | 15.067 | 126.73 |

Tests Between Groups

| Test | Chi Square | DF | Prob>Chi Square |
|---|---|---|---|
| Long-Rank | 0.0693 | 1 | 0.7924 |
| Wilcoxon | 0.0268 | 1 | 0.8700 |

Time to event DFS (months)
Grouped by p4EB-P1 above/below 0.1460276 (node neg)

Summary

| Group | N Failed | N Censored | Mean | Std Error |
|---|---|---|---|---|
| Above | 5 | 0 | 33.4 | 8.66949 |
| Below | 17 | 0 | 100.824 | 8.76975 |
| Combined | 22 | 0 | 85.5 | 9.31989 |

Quantiles

| Group | Median Time | Lower 95% | Upper 95% | 25% Failures | 75% Failures |
|---|---|---|---|---|---|
| Above | 38 | 6 | - | 23 | 44 |
| Below | 102 | 70 | 128 | 75 | 128 |
| Combined | 94 | 47 | 118 | 47 | 123 |

Tests Between Groups

| Test | Chi Square | DF | Prob>Chi Square |
|---|---|---|---|
| Long-Rank | 19.0729 | 1 | <.0001 |
| Wilcoxon | 17.1494 | 1 | <.0001 |

Time to event DFS (months)
Grouped by p4EB-P1 above/below 0.1460276 (node neg)

Summary

| Group | N Failed | N Censored | Mean | Std Error |
|---|---|---|---|---|
| Above | 6 | 0 | 29.6667 | 8.51535 |
| Below | 35 | 0 | 91.2857 | 6.93906 |
| Combined | 41 | 0 | 82.122 | 6.965 |

Quantiles

| Group | Median Time | Lower 95% | Upper 95% | 25% Failures | 75% Failures |
|---|---|---|---|---|---|
| Above | 38 | 5 | - | 6 | 44 |
| Below | 95 | 70 | 118 | 61 | 128 |
| Combined | 85 | 58 | 102 | 44 | 121 |

Tests Between Groups

| Test | Chi Square | DF | Prob>Chi Square |
|---|---|---|---|
| Long-Rank | 23.3664 | 1 | <.0001 |
| Wilcoxon | 21.4551 | 1 | <.0001 |

Survival plot from all cases, both LN⁻ and LN⁺

MTOR PATHWAY THERANOSTIC

This application claims the benefit of U.S. Provisional Application No. 60/727,510, filed Oct. 18, 2005, which disclosure is hereby incorporated by reference in its entirety herein.

BACKGROUND INFORMATION

Human tumors rely on defective protein-based cell signaling processes, driven by post-translational modifications such as protein phosphorylation, to grow, survive and metastasize. These signaling networks are also the targets for most of the current and planned molecular targeted inhibitors. An example is HERCEPTIN, a drug that can block the hyperactive Epidermal Growth Factor (EGF) signaling system in breast cancer. Only patients that have this signaling pathway over-expressed and activated respond to the therapy. An urgent critical need for patient care is to identify patients which will respond to standard therapy and who will require more aggressive therapeutic measures. These more aggressive measures almost always come with increased morbidity, thus are not selected a priori without justification. For example, women with node negative breast cancer and who have estrogen receptor on their tumors are eligible for tamoxifen therapy. However, there are about 30-40% of women who will not respond to tamoxifen therapy, and would require more aggressive treatment—for example with an aromatase inhibitor (AI). Aromatase inhibitors, however, are associated with moderate to severe bone loss, so giving all women AI therapy would be unacceptable. A biomarker that could discriminate outcome and response to therapy would be of great benefit for this example cohort. This conundrum is common to most all of the other human cancers: discrimination of a population that would respond to standard of care from those with poorer prognosis.

Gene expression analysis has indicated an ability to derive prognostic signatures for outcome; however, these endpoints are limited to simple stratification only. The signature cannot tell the physician how to treat the non-responder group; it simply can be used to decide who will respond and who won't. By contrast, protein-signaling profiling can provide a prognostic signature and, importantly, provide information on what therapies to treat the non-responder cohort with. This is because the proteomic portraits are constructed on the drug targets themselves. Furthermore, the analysis of the many genes in gene expression analysis is complex, and generally involves the use of algorithms and extensive computer analysis and does not reflect the activated or functional state of the protein drug targets. Gene expression does not correlate with phosphorylation of signal pathway proteins.

DESCRIPTION OF THE DRAWINGS

FIG. 1 shows characteristics of the Rhabdomyosarcoma sample sets. (FIG. 1A) Two independent study sets, set 1A and 1B, were evaluated by reverse phase protein microarray to profile the state of cellular signaling proteins. (FIG. 1B) Survival analysis of Rhabdomyosarcoma study sets 1A and 1B. Overall survival (OAS) and recurrence free survival (RFS) for both heterogeneous study sets was not significantly different by a Kaplan-Meier survival estimate (OAS log-rank p=0.2111 and RFS p=0.5824). (FIG. 1C) Histological subtype did not show a significant difference between the study sets (Kaplan-Meier OAS log-rank p=0.4103 and RFS p=0.4312).

FIG. 2 shows exploratory data analysis of Rhabdomyosarcoma study set 1A.

FIG. 3 shows reverse phase protein microarray kinase pathway profiling results for Rhabdomyosarcoma sample set 1A. (FIG. 3A) 4EBP1 and 4EBP1 Thr37/46 demonstrated a statistically significant correlation for segregation of non-survivor and survivor status in study set 1A. ((4EBP1 Wilcoxon one-way Chi square 0.0064, df=1, n=32), non-survivor mean 4EBP1=82.4, standard error of the mean=11.48; survivor mean 4EBP1=145.61, standard error of the mean=14.89; (4EBP1 Thr37/46 Chi Square 0.0135, df=1, n=33)). (FIG. 3B) Decision tree analysis indicated 4EBP1 was a discriminator for survival in study set 1A therefore Kaplan-Meier survival estimates for 4EBP1 were calculated. The Kaplan-Meier plots indicated relatively high levels of 4EBP1 (gray line) had a significant statistical correlation with overall survival (Log-rank p<0.0177, n=32 [data not usable for one sample]) and recurrence free survival (p=0.0370) as compared to samples with relatively low 4EBP1 levels (black line).

FIG. 4 shows reverse phase protein microarray kinase pathway profiling results for Rhabdomyosarcoma sample set 1B. (FIG. 4A) Kaplan-Meier survival analysis showed statistically significant correlation in both overall and recurrence free survival by log rank analysis in set 1B for Akt Ser473 (OAS p<0.001, RFS p<0.0009), (FIG. 4B) eIF4G Ser1108 (OAS p<0.0017, RFS p<0.0072), (FIG. 4C) 4EBP1 Thr37/46 (OAS p<0.0110, RFS p<0.0106), and (FIG. 4D) p70S6 Thr 389 (OAS p<0.0085, RFS p<0.0296). The gray line indicates relative high levels of the indicated protein endpoint, the black line represents relative low levels. (FIG. 4E) Protein endpoints evaluated by reverse phase protein microarray for rhabdomyosarcoma sample set 1B (□ survivor status, ■ non-survivor status). 4EBP1 Thr37/46 (p<0.0348), GSK3α/β Tyr279/216 (p<0.0348), eIF4G Ser1108 (p<0.0196), Akt Ser473 (p<0.0227), Bak (p<0.0321), and p70S6 Thr389 (p<0.0373) were found to be statistically significantly associated with overall survival by Wilcoxon one-way analysis (mean±SEM).

FIG. 5 shows IRS-1 cell signaling pathway in Rhabdomyosarcoma study set 1B. (FIG. 5A) IRS-1 feedback loop diagram. IRS-1 is regulated by both a positive feedback loop through Akt and a negative feedback loop through mTOR and p70S6 via IRS-1 ser612. (FIG. 5B) Non-parametric analysis of IRS-1/Akt/mTOR pathway proteins in sample set 1B (Table 1B). Spearman's Rho table of selected prosurvival and apoptotic signaling proteins evaluated for sample set 1B. (FIG. 5C) Spearman's Rho non-parametric analysis showed a correlation between IRS-1 Ser612 and mTOR Ser2448 for tumors from patients with survivor status (p=0.0027) compared to tumors from patients with non-survivor status (p=0.7358). (FIG. 5D) Similar correlations were noted between IRS-1 Ser612 and p70S6 Thr389 for tumor samples from patients with survivor status (p=0.00004) versus tumor samples from patients with non-survivor status (p=0.1827).

FIG. 6 shows CCI-779 suppression of human rhabdomyosarcoma tumor growth in a mouse xenograft model. (FIG. 6A) Time dependent CCI-779 inhibition of phosphorylation of mTOR pathway downstream substrates within tumor tissue in a xenograft treatment model. CCI-779 inhibited phosphorylation of mTOR pathway substrates, pS6 Ser235/236 and 4EBP1 Thr70 in both non-involved muscle and tumor tissue as compared to actin. (FIG. 6B) CCI-779 inhibited tumor growth in Rh30 and RD mouse xenograft models. $2\times10^6$ cells in 0.2 mL total volume per mouse, from either Rh30 alveolar or RD embryonal cell lines, were injected orthotopically into the left hind leg gastrocnemius muscle of a SCID beige murine model. After 1 week, mice were assigned to control (n=8) or CCI-779 treatment groups (n=8). Tumor volume, as measured with calipers, was less in the CCI-779 treatment group as compared to the vehicle alone for both the Rh30 and RD xenografts --▲-- RD control, -■- Rh30 plus CCI-779, -- ♦-- Rh30 control --X- RD plus CCI-779, (RD p=0.00008; Rh30 p=0.0002, Student's t-test). (FIG. 6C) CCI-779 was administered at 20 mg/kg/IP every 3 days for 30 days. Protein extracts from Rh30 and RD mouse xenograft tumors or uninvolved muscle were treated with CCI-779 or vehicle for 30 days and analyzed by Western blotting for S6 and 4EBP1 phosphorylation. CCI-779 suppresses phosphorylation of 4EBP1 in both Rh30 and RD muscle and tumor cells.

DESCRIPTION OF THE INVENTION

Figure 2A:
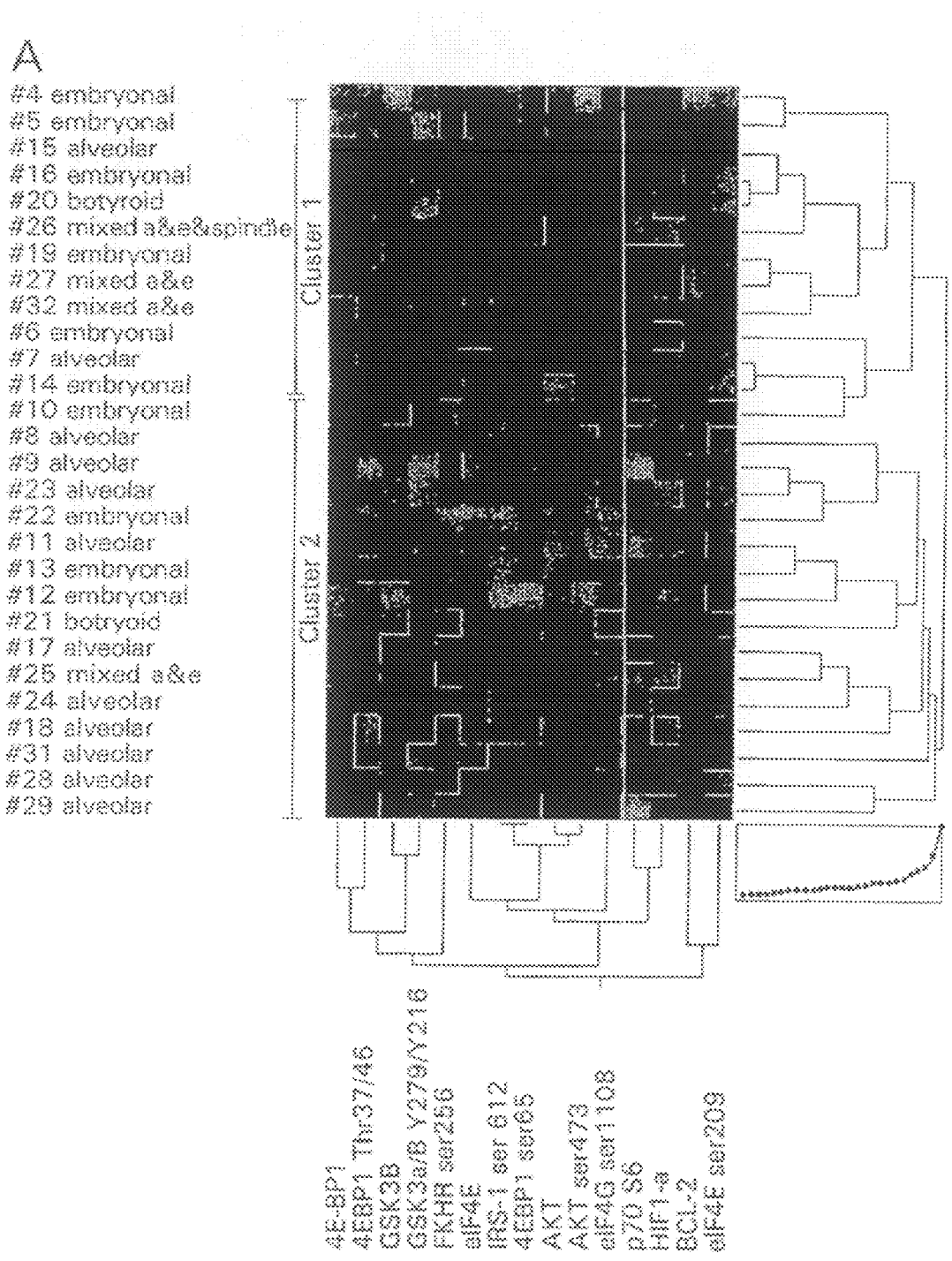
(FIG. 2A) Unsupervised Bayesian clustering of normalized protein endpoints (columns) indicated two major clusters of tumors (rows). These clusters appear unrelated to clinical parameters in (FIG. 2B). The two clusters were compared by Fisher's exact test, p>0.05.

The present invention provides, e.g., combinations and methods for treating cancer based on assessing the activation state of one or more members of the mTOR signaling pathway, and genes and their encoded products which interconnect with this pathway. Because a diagnostic assay of the invention requires the determination of the phosphorylation state of only a few proteins, the assay is simple to conduct and does not require complex, computer-based analysis.

The invention relates, e.g., to a method for predicting a subject's response to a chemotherapeutic agent and/or the subject's prognosis, and/or for treating a cancer in a subject in need thereof, comprising measuring the phosphorylation state of at least one member of the mTOR pathway, and/or of at least one member of an interconnected polypeptide pathway, compared to a baseline value, in a cancer tissue or cancer cell sample from the subject, wherein an elevated level of the phosphorylation state compared to the baseline value indicates that the subject is a non-responder to the chemotherapeutic agent and/or has a poor prognosis.

As used herein, a "response to a therapeutic agent" refers to a response to a conventional chemotherapeutic agent, such as those listed elsewhere herein. This term does not include a response to the new class of cancer inhibitors described herein: inhibitors of the mTOR pathway, or of one of the interconnected pathways discussed herein.

A "subject," as used herein, includes any animal that has a cancer. Suitable subjects (patients) include laboratory animals (such as mouse, rat, rabbit, or guinea pig), farm animals, and domestic animals or pets (such as a cat or dog). Non-human primates and, preferably, human patients, are included.

The "phosphorylation state" of a protein refers to the degree of (total amount of) phosphorylation of the protein. This includes both the number of sites (e.g. suitable Ser, Thr or Tyr amino acid residues) of the protein that are phosphorylated, and the level of phosphorylation at any given acceptor site on the amino acid chain.

A "baseline value," as used herein, refers to the level of phosphorylation of the same protein in a normal, non-cancerous, or unstimulated subject. An increase in the amount of phosphorylation of a protein can reflect either an increase in the number of suitable amino acid residues of the protein (e.g., serines, threonines or tyrosines) that are phosphorylated, or an increased frequency of phosphorylations at a particular amino acid residue. For example, a baseline value includes reference standards, where a predetermined threshold value (or range of values) determines whether the amount of measured phosphoprotein, or the phosphorylation state of the protein, is above the "normal" value. The terms threshold level and baseline value are used interchangeably herein. For each protein whose level of phsophorylation is determined, the value can be normalized to the total protein in the cell; or to the amount of a constitutively expressed protein (from a housekeeping gene), such as actin; or the amount of a phosphoprotein may be compared to the amount of its non-phosphorylated counterpart.

The "interconnected" polypeptide pathway may be from the Akt pathway, the IRS pathway, or it may be another interconnected polypeptide, such as pRb, substrates of Akt (such as GSK3), or modulators of apoptosis (such as Bak). The phosphorylation state may be measured from any individual member of one of the mentioned pathways, or from combinations thereof. For example, if at least one member of the mTOR pathway is coded as "A," at least one member of the Akt pathway as "B," and at least one member of the IRS pathway as "C," the phosphorylation state that is measured may be of A; B; C; A+B; A+C; B+C; or A+B+C.

The pathway member may be, e.g., Akt-kinase, mTOR, 4E-BP1/PHAS-1, p70s6k, eIF-4E, or eIF4G, PTEN, PDK1, GSK3Beta, TSC1/2, ILK, Gab1/2, p27Kip1, FKHR, FKHRL, eNOS, ASK1, BAD, pRAS40, 14-3-3, or CHK1. Specific phosphorylation residues are indicated elsewhere herein. In another embodiment, the inhibitor binds to FKB12.

Another aspect of the invention is a method as above, which is a treatment method, further wherein, if no significant increase in phosphorylation state is observed compared to the baseline value in the member of the pathway, the subject is treated with a conventional method of chemotherapy.

Another aspect of the invention is a method as above, which is a treatment method, further wherein, if a significantly increased amount of phosphorylation compared to the baseline is observed in the member of the pathway, an inhibitor of the mTOR pathway or of an interconnected polypeptide pathway is administered to the subject.

A "significant" increase, as used herein, means a statistically significant change, using statistical methods that are appropriate and well-known in the art, generally with a probability value of less than five percent chance of the change being due to random variation. As used herein, the singular forms "a," "an" and "the" include plural referents unless the context clearly dictates otherwise. For example, "a" member of the tested pathway, as used above, includes 2, 3, 4, 5 or more members of the pathway. Similarly, "an" inhibitor of the pathway includes multiple inhibitors.

In embodiments of the invention, a conventional chemotherapeutic agent may be administered to the subject in combination with the inhibitor. The conventional chemotherapeutic agent may be administered together with (concurrently with) the inhibitor of a member of the mTOR or interconnected pathway; or it may be administered at a suitable time after the inhibitor of the mTOR/interconnected pathway is administered (e.g. after the level of phosphorylation is decreased to a "normal" level).

In aspects of the invention, the phosphorylation state of the pathway member is measured after administration of the inhibitor; and/or the amount of inhibitor administered is effective to decrease the amount of phosphorylation of the pathway member.

Another aspect of the invention is in a method of treating a cancer with a chemotherapeutic agent in a subject in need thereof, the improvement comprising administering an inhibitor of the mTOR pathway or of an interconnected polypeptide pathway, if increased phosphorylation is measured in a member of the mTOR pathway or of an interconnected polypeptide pathway in a cancer tissue or cancer cell sample from the treated subject.

Another aspect of the invention is a method of treating a cancer which is resistant or refractory to a chemotherapeutic agent, comprising administering an inhibitor of the mTOR pathway or of an interconnected polypeptide pathway, if increased phosphorylation is measured in a member of the mTOR pathway or of an interconnected polypeptide pathway in a cancer tissue or cancer cell sample from the treated subject.

In a treatment method of the invention, the phosphorylation may be measured prior to chemotherapy, and when increased phosphorylation is measured in a member of the pathway in a cancer tissue or cancer cell sample from the treated subject, the inhibitor is administered in combination with a therapeutic agent for treating the cancer. In treatment methods of the invention, the phosphorylation of the pathway member may be measured using an antibody to the phosphorylation site of at least one member selected from, e.g., PI3-kinase, Akt-kinase, mTOR, 4E-BP1/PHAS-1, p70s6k, eIF-4E, and eIF-4G. The cancer may be, e.g., a breast cancer, rhabdomyosarcoma, or lung cancer (such as non-small cell lung cancer). In embodiments of the invention, the sample comprises metastatic cells; and/or it is not associated with a loss of function of PTEN and/or a mutated and activated Akt.

Another aspect of the invention is a method of predicting a subject's response to a chemotherapeutic agent and/or the subject's prognosis, comprising measuring changes in the amount or phosphorylation state of at least one member of the Akt/mTOR pathway (or interconnected genes and their encoded polypeptides) in a cancer tissue or cancer cell sample from the treated subject, whereby elevated levels indicate that the subject is a non-responder to the chemotherapeutic agent and/or has a poor prognosis.

Another aspect of the invention is in a method of treating rhabdomyosarcoma with a chemotherapeutic agent in a subject in need thereof, the improvement comprising administering CCI-779, when increased phosphorylation is measured at 4EBP1 Thr37/46, eIF-4G ser1108, and/or p70S6 Thr389 in a cancer tissue or cancer cell sample from the treated subject.

Another aspect of the invention is a kit for predicting a subject's response to a chemotherapeutic agent and/or the subject's prognosis, comprising one or more agents for detecting the phosphorylation state of at least one member of the mTOR pathway, at least one member of the Akt pathway, and/or at least one member of the IRS pathway, or a combination thereof. The agents can be, e.g., antibodies specific for phosphorylated forms of the proteins. The kit may include agents suitable for a label or label-free method known in the art to measure phosphorylation sites using mass spectrometry or electrophoretic mobility.

Another aspect of the invention is a pharmaceutical composition, or a kit for treating a subject in need thereof, comprising an inhibitor of at least one member of the mTOR pathway, and/or an inhibitor of at least one member of the Akt pathway, and/or an inhibitor of at least one member of the IRS pathway, or a combination thereof. Pharmaceutical compositions comprise a pharmaceutically acceptable carrier. The pharmaceutical agent or kit may further comprise a chemotherapeutic agent that can be administered in conjunction with the inhibitors of the invention.

Another aspect of the invention is a pharmaceutical composition or kit for treating a patient whose cancer is resistant or refractory to a chemotherapeutic agent, comprising an inhibitor of at least one member of the mTOR pathway, and/or an inhibitor of at least one member of the Akt pathway, and/or an inhibitor of at least one member of the IRS pathway, or a combination thereof. The pharmaceutical composition or kit may further comprise a chemotherapeutic agent that can be administered in conjunction with, or in series with, the inhibitors.

The mTOR signaling pathway includes any members or components that participate in its signal transduction cascade. These include, but are not limited to, mTOR (mammalian target of rapamycin; also known as FRAP, RAFT1, or RAPT1), RAPTOR (regulatory associated protein of mTOR), 4E-BP1/PHAS-1, p70s6k, TSC (tuberous sclerosis complex), 4E-BP1/PHAS-1, p70s6k, eIF-4E, eIF-4G, and/or eIF4E complex. Genes (or their encoded products) that are interconnected with (interact with) the mTOR pathway include, but are not limited to, members of the Akt pathway [e.g. Akt, PI3-kinase, PTEN (phosphatase and tensin homolog) and FKBP12]; members of the IRS pathway [e.g. IRS-1 and insulin growth factor (IGF) receptors, including IGF-R1, IGF-Rβ, and IGF-Rα]; and members of other inter-related pathways [e.g. pRb (the tumor suppressor, retinoblastoma protein); substrates of Akt, such as GSK3; and modulators of apoptosis, such as Bak]. These pathways, including polypeptides which interact with members of the mTOR pathway, are sometimes collectively referred to herein as "mTOR or interconnected polypeptide pathways."

Preferred activated members which are hyperphosphorylated (e.g., more than normal) and the position at which they are phosphorylated include, e.g., 4E-BP1 Thr37/46; eIF-4E ser1108; AKT ser473; p70s6k Thr389, etc. One or more of these can be used in accordance with the present invention.

The nucleotide and amino acid sequences of the above-mentioned genes are well-known and can be determined routinely, as well as downloaded from various known databases. See, e.g., www.ncbi.nlm.nih.gov.

The activation of an mTOR or interconnected signaling pathway can be measured using any suitable method, e.g., methods that enable the measurement of total phosphorylated protein or the degree of phosphorylation of a protein. Among the many types of suitable assays are colorimetric assays, immunoassays (such as immunohistochemistry, ELISAs, etc.), assays based on fluorescent readouts, suspension bead assays, etc. For example, protein measurements (e.g., measurement of phosphorylated proteins) can be made using reverse phase protein microarrays (RPMA). See, e.g., Nishizuka et al. (2003) *Proc. Natl. Acad. Sci.* 100, 14229-14239. Antibodies suitable for use in such assays are commercially available, or can be prepared routinely, including antibodies to the phosphorylated and unphosphorylated forms of the polypeptide. (Of particular usefulness are antibodies that have been developed to specifically recognize the phosphorylated isoform of kinase substrates.) In addition, Western blot, ELISA assays, immunoprecipitation, and mass spectroscopy, and other conventional assays can be used to assess the level and/or degree of phosphorylation of, e.g., an mTOR signaling pathway member. Suitable methods include those that can detect the phosphoprotein in a very small sample (e.g. about 200 cells). Alternatively, methods can be used that are suitable for a large sample size (e.g. about 20,000-25,000 cells).

An mTOR inhibitor (or an inhibitor of an interconnected pathway) can be administered when an increased total amount of phosphoprotein, or the degree of phosphorylation, is observed in at least one member of the mTOR pathway (or the interconnected pathway) in the cancer sample obtained from the subject.

Increased amounts of total protein or phosphorylated protein can be determined routinely. For example, reference standards can be used, where a predetermined threshold value (or range of values) determines whether the amount of measured protein is above the "normal" value. Such a threshold value is sometimes referred to herein as a baseline value. In addition, the amounts can be determined by intensity, where a scoring intensity is used to determine whether the subject's Akt/mTOR pathway is activated. (For example, using a 1 to 5 scoring system, where 5 is highest, and an intensity over 3 indicates pathway activation).

Aspects of the invention can be utilized as a prognostic and/or diagnostic to predict a subject's response to a chemotherapeutic agent and/or prognosis. Such a method can involve measuring changes in the amount and/or phosphorylation state of at least one member of the mTOR and/or interconnected pathway in a cancer tissue or cancer cell sample from a treated subject, whereby elevated levels indicate that the subject is a non-responder to a chemotherapeutic agent which is typically used to treat the cancer and/or has a poor prognosis.

Akt/mTOR inhibitors include, but are not limited to the following:

Examples of phosphatidylinositol-3-kinase (PI3-kinase) inhibitors, include, but are not limited to, e.g., celecoxib and analogs thereof, such as OSU-03012 and OSU-03013 (e.g., Zhu et al. (2004) *Cancer Res.* 64(12):4309-18);

3-deoxy-D-myo-inositol analogs (e.g., U.S. Application No. 20040192770; Meuillet et al. (2004) *Oncol. Res.* 14, 513-27, 2004), such as PX-316;

2'-substituted, 3'-deoxy-phosphatidyl-myo-inositol analogs (e.g., Tabellini et al. (2004) *Br. J. Haematol.* 126(4), 574-82);

fused heteroaryl derivatives (U.S. Pat. No. 6,608,056);

3-(imidazo[1,2-a]pyridin-3-yl) derivatives (e.g., U.S. Pat. Nos. 6,403,588 and 6,653,320);

Ly294002 (e.g., Vlahos et al. (1994) *J. Biol., Chem.* 269(7), 5241-5248);

quinazoline-4-one derivatives, such as IC486068 (e.g., U.S. Application No. 20020161014; Geng et al. (2004) *Cancer Res.* 64, 4893-99);

3-(hetero)aryloxy substituted benzo(b)thiophene derivatives (e.g., WO 04 108715; also WO 04 108713);

viridins, including semi-synthetic viridins such as PX-866 (acetic acid (1S,4E,10R,11R,13S,14R)-[4-diallylaminomethylene-6-hydroxy-1-methoxymethyl-10,13-dimethyl-3,7,17-trioxo-1,3,4,7,10,11,12,13,14,15,16,17-dodecahydro-2-oxa-cyclopenta[a]phenanthren-11-yl ester) (e.g., Ihle et al. (2004) *Mol Cancer Ther.* 3(7), 763-72; U.S. Application No. 20020037276; U.S. Pat. No. 5,726,167); and wortmannin and derivatives thereof (e.g., U.S. Pat. Nos. 5,504,103; 5,480,906, 5,468,773; 5,441,947; 5,378,725; 3,668,222).

Examples of Akt-kinase (also known as protein kinase B) inhibitors include, but are not limited to, e.g., Akt-1-1 (inhibits Akt1) (Barnett et al. (2005) *Biochem. J.*, 385 (Pt. 2), 399-408);

Akt-1-1,2 (inhibits Ak1 and 2) (Barnett et al. (2005) *Biochem. J.* 385 (Pt. 2), 399-408);

API-59CJ-Ome (e.g., Jin et al. (2004) *Br. J. Cancer* 91, 1808-12);

1-H-imidazo[4,5-c]pyridinyl compounds (e.g., WO05011700);

indole-3-carbinol and derivatives thereof (e.g., U.S. Pat. No. 6,656,963; Sarkar and Li (2004) *J Nutr.* 134(12 Suppl), 3493S-3498S);

perifosine (e.g., interferes with Akt membrane localization; Dasmahapatra et al. (2004) *Clin. Cancer Res.* 10(15), 5242-52, 2004);

phosphatidylinositol ether lipid analogues (e.g., Gills and Dennis (2004) *Expert. Opin. Investig. Drugs* 13, 787-97);

triciribine (TCN or API-2 or NCI identifier: NSC 154020; Yang et al. (2004) *Cancer Res.* 64, 4394-9).

Examples of mTOR inhibitors include, but are not limited to, e.g.,

FKBP12 enhancer;

rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl)rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. No. 5,118,677, U.S. Pat. No. 5,118,678, U.S. Pat. No. 5,100,883, U.S. Pat. No. 5,151,413, U.S. Pat. No. 5,120,842, WO 93/111130, WO 94/02136, WO 94/02485, WO 95/14023, WO 94/02136, WO 95/16691, WO 96/41807, WO 96/41807 and U.S. Pat. No. 5,256,790;

phosphorus-containing rapamycin derivatives (e.g., WO 05016252);

4H-1-benzopyran-4-one derivatives (e.g., U.S. Provisional Application No. 60/528,340).

Examples of IRS pathway inhibitors include, but are not limited to, the following: Specific IGF-IR inhibition with neutralizing antibody, antagonistic peptide, or the selective kinase inhibitor NVP-ADW742 has been demonstrated to have activity against diverse tumor cell types. Proteasome inhibitors, MG132 and lactacystin inhibit IRS-1 phosphorylation. Proteasome inhibitors can regulate the tyrosine phosphorylation of IRS-1 and the downstream insulin signaling pathway, leading to glucose transport. Inducible nitric oxide synthase, iNOS and NO donors induce IRS degradation. Serine phosphorylation of IRS-1 is regulated by the inhibitor of kappa B kinase complex. Thapsigargin down-regulates IRS-1. PKC pathway and Akt inhibitors include Calphostin C, Staurosporine, and LY294002. STI571 is a further inhibitor of the cKit pathway related to the pathways of the present invention.

Examples of compounds in preclinical or clinical use, include, e.g., AP23573, AP23841, CCI-779, and RAD001.

Any tumor or cancer can be treated in accordance with the present invention irrespective of the mechanism that is responsible for it. This includes tumors or cancers of any organ, including but are not limited to, e.g., colon, pancreas, breast, prostate, bone, liver, kidney, lung, testes, skin, pancreas, stomach, prostate, ovary, uterus, head and neck, blood cell, lymph, etc.

Cancers that can be treated in accordance with the present invention include, but are not limited to, brain tumors, breast cancer, bone sarcoma (e.g., osteosarcoma and Ewings sarcoma), bronchial premalignancy, endometrial cancer, glioblastoma, hematologic malignancies, hepatocellular carcinoma, Hodgkin's disease, kidney neoplasms, leukemia, leimyosarcoma, liposarcoma, lymphoma, Lhermitte-Duclose disease, malignant glioma, melanoma, malignant melanoma, metastases, multiple myeloma, myeloid metaplasia, myeloplastic syndromes, non-small cell lung cancer, pancreatic cancer, prostate cancer, renal cell carcinoma (e.g., advanced, advanced refractory), rhabdomyosarcoma, soft tissue sarcoma, squamous epithelial carcinoma of the skin, Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell carcinoma, non-small-cell lung carcinoma, bronchial adenoma, and pleuropulmonary blastoma.

Examples of brain cancers include, but are not limited to, brain stem and hypophtalmic glioma, cerebellar and cerebral astrocytoma, medulloblastoma, ependymoma, and neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small intestine, and salivary gland cancers.

Tumors of the urinary tract include, but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, and/or oropharyngeal cancers, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

Cancers can also be excluded from the present invention, e.g., cancers associated with loss of function of PTEN; mutated and activated Akt (e.g. PTEN null tumors and tumors with ras mutations); or other mutations in the mTOR or interconnected inhibitors pathway which have been identified as the primary causative gene or polypeptide responsible for the cancer.

Therapeutic methods can involve:

A: Measurement of the activation state of the mTOR signal pathway and/or interconnections with other signal pathways in a tumor sample. Activation can be assessed by phosphorylation (and/or total amounts) of pathway members which regulate positive and negative regulation of upstream and downstream signals. B: Based on the signal pathway activation pattern, administration of a therapy to block the activation of the pathway as a stand alone therapy or as a therapy used in a neo-adjuvant or combination therapy protocol.

One aspect of the invention is a diagnostic or prognostic test for cancer employing phosphorylated protein members of the mTOR pathway. Example analytes are discussed elsewhere herein. It has been discovered, as shown in the Examples, that the activation of the mTOR pathway or an interconnected pathway can predict outcome in lung, breast and rhabdomyosarcoma patients who have been treated with the current standard of care. For example, the proteins, mTOR, 4EBP1, E1F4G, E1F4E, and p70S6 can, in their phosphorylated state, correlate with outcome. The activation of other pathways was not observed to be so correlated. Simply put, patients with the mTOR pathway activated, as evidenced by the phosphorylation levels of downstream substrates of mTOR, have shorter survival, disease free intervals, or other measures of therapeutic success compared to patients that do not have mTOR activation. This standard of care would include surgery, chemotherapy and estrogen receptor therapy (breast). Since these tumor types represents a disparate pathological lineage arising from different microenvironments, it could be expected that this discovery would be useful for other tumor types or tumor stem cells derived therefrom, including as carcinomas: colorectal, prostate, ovarian, breast, lung, ovary, brain, thyroid, kidney and sarcomas: fibrosarcomas, angiosarcomas, and melanomas, etc.

Aspects of the invention also include treating subjects having cancer who have become resistant or refractory to a chemotherapeutic treatment. By the latter, it is meant that a patient who has previously responded to a treatment with at least one chemotherapeutic, after being exposed to the agent, shows no or only weak anti-cancer (e.g., anti-proliferative response, such as no, or only weak, inhibition of tumor growth) after subsequent treatments with such an agent. Thus, after a patient has been treated with a chemotherapeutic agent with success, but subsequent treatments show no or little affect, the cancer can be described as being refractory or resistant to the agent. The method involves identifying such patients, and then determining whether they have elevated mTOR pathway activation. This population could be treated mTOR inhibitors (or inhibitors of a downstream, upstream, or both downstream and upstream, interconnected pathway).

In one embodiment of the invention, a subject is treated with one or more inhibitors that are targeted to a specific node in an mTOR or interconnected pathway (e.g. an mTOR or AKT-specific inhibitor). In another embodiment, a combination of inhibitors is used to inhibit multiple nodes in the pathway. This sometimes allows for the administration of lower doses of the inhibitors, with less toxicity, and disrupts multiple points along a pathway. Such an approach can be useful, for example, if several proteins exhibit increased phosphorylation.

Examples of chemotherapeutic agents to which a patent can become refractory or acquire resistance include, e.g., but are not limited to, e.g., alkylating agents (e.g., cyclophosphamide, ifosfamide, melphalan, chlorambucil, aziridines, epoxides, alkyl sulfonates), cisplatin and its analogues (e.g., carboplatin, oxaliplatin), antimetabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., vinca alkaloids, such as vincristine, vinblastine, and vinorelbine; taxanes, such as paclitaxel and docetaxel), interferons, interleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemestane, octreotide), octreotide, anti-androgens (e.g., flutamide, casodex), kinase and tyrosine inhibitors (e.g., imatinib (STI571 or Gleevac); gefitinib (Iressa); and erlotinib (Tarceva), etc. See, e.g. Cancer: Principles and Practice of Oncology, 7th Edition, Devita et al, Lippincott Williams & Wilkins, 2005, Chapters 15, 16, 17, and 63.

The inventors have found that subjects resistant (refractory) to a variety of chemotherapeutic agents, having different mechanisms of action, all exhibit activation of the mTOR or interconnected pathways. Therefore, it could be expected that the activation of one or more of these pathways would apply to cancers that are resistant to a variety of chemotherapeutic agents other than the ones exemplified herein.

The Examples show that, in an animal xenograft model, the administration of an mTOR inhibitor suppressed downstream phosphorylation of proteins within the mTOR pathway and greatly reduced the growth rate of two different RMS lines compared to controls. This supports the therapeutic usefulness of mTOR inhibitors, and inhibitors of interconnected genes/proteins.

Thus, the present invention is both a prognostic signature as well as a new drug target. This is now referred to as a "theranostic"—where the measured analytes serve both as a diagnostic as well as a therapeutic target. A current example of this is e-erbB2. This protein, a member of the EGF receptor family, is measured in breast cancer patients as a diagnostic endpoint for patients with poor prognosis, but is a drug target itself—for HERCEPTIN. Thus it serves to stratify and target therapy.

Biopsy or other tissue or cell samples (including blood samples and samples from metastatic sites) can be analyzed for the following endpoints that relate specifically to mTOR (or interconnected) pathway activation:

Total MTOR
Total 4EBP1
Total EIF4G
Total E1F4E
Total p70S6
Phosphorylated pAKT
Phosphorylated mTOR
Phosphorylated 4EBP1
Phosphorylated EIF4G
Phosphorylated E1F4E
Phosphorylated p70S6

Combinations of intensities values of these specific endpoints, or other pathway members, can be used to stratify patients to received standard of care or who would receive a regimen of an mTOR inhibitor (and/or an inhibitor of an interconnected pathway), such as, but not limited to, CCI-779, a rapamycin inhibitor.

The mentioned proteins in their unphosphorylated and phosphorylated states can be used in accordance with the present invention, irrespective of the mechanism of action. Thus, although it is believed that the mechanism is via the mTOR pathway, the present invention is not bound to any mechanism by which the theranostic, therapeutic, and/or prognostics methods achieve their success.

The inhibitors discussed herein can be formulated into various compositions, e.g., pharmaceutical compositions, for use in therapeutic treatment methods. The pharmaceutical compositions can be assembled as a kit. Generally, a pharmaceutical composition of the invention comprises an anticancer-effective amount of the inhibitor. An "anticancer effective amount," as used herein, is an amount that is sufficient to effect at least a therapeutic response in the individual over a reasonable time frame. For example, it can ameliorate, at least to a detectable degree, the symptoms of a cancer, or can inhibit the growth of a tumor, etc.

The composition can comprise a carrier, such as a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

A pharmaceutical composition or kit of the invention can contain other pharmaceuticals (such as chemotherapeutic agents), in addition to the inhibitor(s) of a member of the mTOR or interconnected pathway. The other chemotherapeutic agent(s) can be administered at any suitable time during the treatment of the patient, either concurrently or sequentially For example, in one embodiment, the other chemotherapeutic agent(s) are administered at a time after treatment with an inhibitory agent of the invention has significantly reduced the activation of the mTOR pathway in a subject. In another embodiment, the other chemotherapeutic agent is administered at the same time as (concurrently with) the mTOR, etc. inhibitor. In one embodiment, the other chemotherapeutic agent is one of the agents noted above to which a subject can become refractory or acquire resistance. In another embodiment, other chemotherapeutic agents can be used, representative examples of which are listed in Table 2.

One skilled in the art will appreciate that the particular formulation will depend, in part, upon the particular inhibitory agent of the invention, or other chemotherapeutic agent, that is employed, and the chosen route of administration. Accordingly, there is a wide variety of suitable formulations of compositions of the present invention.

TABLE 2

| Mechanism of action | Class (drug names) |
| --- | --- |
| Alkylating agents | Nitrogen mustards: (Chlorambucil, Chlormethine, Cyclophosphamide, Ifosfamide, Melphalan). Nitrosoureas: (Carmustine, Fotemustine, Lomustine, Streptozocin). Platinum: (Carboplatin, Cisplatin, Oxaliplatin, BBR3464). Busulfan, Dacarbazine, Mechlorethamine, Procarbazine, Temozolomide, ThioTEPA, Uramustine |

TABLE 2-continued

| Mechanism of action | Class (drug names) |
| --- | --- |
| Antimetabolites: | Folic acid: (Methotrexate, Pemetrexed, Raltitrexed). Purine: (Cladribine, Clofarabine, Fludarabine, Mercaptopurine, Tioguanine). Pyrimidine: (Capecitabine). Cytarabine, Fluorouracil, Gemcitabine |
| Plant alkaloids: | Taxane: (Docetaxel, Paclitaxel). Vinca: (Vinblastine, Vincristine, Vindesine, Vinorelbine). |
| Cytotoxic/antitumor antibiotics: | Anthracycline family: (Daunorubicin, Doxorubicin, Epirubicin, Idarubicin, Mitoxantrone, Valrubicin). Bleomycin, Hydroxyurea, Mitomycin |
| Topoisomerase inhibitors: | Topotecan, Irinotecan, Podophyllum: (Etoposide, Teniposide). |
| Monoclonal antibodies: | Alemtuzumab, Bevacizumab, Cetuximab, Gemtuzumab, Panitumumab, Rituximab, Trastuzumab |
| Photosensitizers: | Aminolevulinic acid, Methyl aminolevulinate, Porfimer sodium, Verteporfin |
| Other: | Alitretinoin, Altretamine, Amsacrine, Anagrelide, Arsenic trioxide, Asparaginase, Bexarotene, Bortezomib, Celecoxib, Denileukin diftitox, Erlotinib, Estramustine, Gefitinib, Hydroxycarbamide, Imatinib, Pentostatin, Masoprocol, Mitotane, Pegaspargase, Tretinoin |
| Hormones | Tamoxafin, Progesterones |

Formulations suitable for oral administration can consist of liquid solutions, such as an effective amount of the agent dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g. intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitory agents of the invention, alone or in combination with other chemotherapeutic agents, can be made into aerosol formulations to be administered via inhalation. These aerosol formulations can be placed into pressurized acceptable propellants, such as dichlorodifluoromethane, propane, nitrogen and the like.

The inhibitory agent of the invention, alone or in combinations with other chemotherapeutic agents, can be made into suitable formulations for transdermal application and absorption (Wallace et al., 1993, supra). Transdermal electroporation or iontophoresis also can be used to promote and/or control the systemic delivery of the agents and/or pharmaceutical compositions of the present invention through the skin (e.g., see Theiss et al. (1991), *Meth. Find. Exp. Clin. Pharmacol* 13, 353-359).

Formulations which are suitable for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

One skilled in the art will appreciate that a suitable or appropriate formulation can be selected, adapted or developed based upon the particular application at hand.

Dosages for an inhibitory agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other chemotherapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired anti-cancer effective amount or effective concentration of the agent in the individual patient. One skilled in the art also can readily determine and use an appropriate indicator of the "effective concentration" of the compounds of the present invention by a direct or indirect analysis of appropriate patient samples (e.g., blood and/or tissues).

The dose of an inhibitory agent of the invention, or composition thereof, administered to an animal, particularly a human, in the context of the present invention should be sufficient to effect at least a therapeutic response in the individual over a reasonable time frame (an anti-cancer effective amount). The exact amount of the dose will vary from subject to subject, depending on the species, age, weight and general condition of the subject, the severity or mechanism of any disorder being treated, the particular agent or vehicle used, its mode of administration and the like. The dose used to achieve a desired anticancer concentration in vivo will be determined by the potency of the particular inhibitory agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

When given in combined therapy, the other chemotherapeutic agent, for example, can be given at the same time as the inhibitor, or the dosing can be staggered as desired. The two drugs also can be combined in a composition. Doses of each can be less when used in combination than when either is used alone.

Another embodiment of the invention is a kit useful for any of the methods disclosed herein; such a kit comprises one or more inhibitors discussed herein (e.g. for a diagnostic or therapeutic method). For example, a kit suitable for therapeutic treatment of a cancer in a subject may further comprise a pharmaceutically acceptable carrier and, optionally, a container or packaging material. Among other uses, kits of the invention can be in experimental applications. A skilled worker will recognize components of kits suitable for carrying out any of the methods of the invention.

Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

In the foregoing and in the following examples, all temperatures are set forth in uncorrected degrees Celsius; and, unless otherwise indicated, all parts and percentages are by weight.

EXAMPLES

Example I

Phosphoprotein Pathway Mapping: Akt/mTOR Activation is Negatively Associated with Childhood Rhabdomyosarcoma Survival A. Introduction Rhabdomyosarcoma (RMS) arises from undifferentiated mesenchymal cells bearing skeletal muscle features. RMS is the most common soft tissue sarcoma in children, consisting of three histological subtypes—alveolar, embryonal and botyroid. Despite the recent advances in combination chemotherapy, and the molecular knowledge of the translocations t(2;13)(q35;q14) and t(1;13)(p36;q14) in alveolar RMS, the overall survival of all patients with childhood rhabdomyosarcoma has remained in the range of 60-70%.

In several published studies on treatment regimens for RMS, the overall disease free survival rate was only 67%. Unfortunately, there is no way to identify the 33% of children destined to fail initial therapy, regardless of disease stage or histological subtype. On the other hand, the 60-70% of children that respond to standard therapy do so exceedingly well, with a vast majority of these patients currently living disease free. Consequently, an urgent clinical goal is to identify functionally important molecular networks associated with the 30-40% non-responder RMS subjects in order to develop new treatment strategies for this group.

B. Materials and Methods

1. Specimens and patient data. All specimens (n=59) and relevant clinical data were obtained from the Intergroup Rhabdomyosarcoma Study (IRS) IV, D9502 and D9803 studies from the Children's Oncology Group with appropriate IRB approval.

All specimens were snap frozen in liquid nitrogen and procured prior to therapy. The sample set was analyzed in two groups, 1A and 1B (FIG. 1A). FIG. 1B shows the survival characteristics for the two study sets. Samples were anonymized and blinded as to clinical survival outcome prior to final data analysis. The samples representing the study set 1A (FIG. 1A) consisted of nine snap frozen surgical specimens and 290 frozen section slides for 33 different patients with a pathological diagnosis of rhabdomyosarcoma. All patients used here had stage 3 (tumors <5 cm or regional lymph node involvement) disease and Group III tumors (gross residual disease remaining following treatment) prior to study entry. An additional set of 46 frozen section samples and clinical data were provided by the COG for patients from the same protocols (FIG. 1A, Table 1B). Pathologic diagnosis was rendered prior to therapy. An independent board-certified pathologist verified the diagnosis prior to Laser Capture Microdissection. The histological subtypes represented alveolar, embryonal, botryoid and mixed morphologic types. Pure tumor cell populations were microdissected from the tissue sections with a PixCell II (Molecular Devices, Sunnyvale, Calif.).

2. Reverse Phase Protein Microarrays. Microdissected cells, generated by previously published methods (e.g. Petricoin et al. (2005), *J. Clin Oncol* 23, 3614-3621; Liotta et al. (2003) *Cancer Cell* 3, 317-325; Sheehan et al. (2005) *Mol Cell Proteomics* 4, 346-365) were subjected to lysis and reverse phase protein microarrays were printed in duplicate with the whole cell protein lysates as described by Sheehan et al. (2005), supra. Briefly, the lysates were printed on glass backed nitrocellulose array slides (FAST Slides Whatman, Florham Park, N.J.) using a GMS 417 arrayer (Affymetrix, Santa Clara, Calif.) equipped with 500 µm pins. Each lysate was printed in a dilution curve representing neat, 1:2, 1:4, 1:8, 1:16 and negative control dilutions. The slides were stored with desiccant (Drierite, W. A. Hammond, Xenia, Ohio) at −20° C. prior to immunostaining.

3. Protein Microarray Immunostaining. Immunostaining was performed on an automated slide stainer per manufacturer's instructions (Autostainer CSA kit, Dako, Carpinteria, Calif.). Each slide was incubated with a single primary antibody at room temperature for 30 minutes. Polyclonal primary antibodies were: GSK3α/β Tyr279/216 (Invitrogen-Biosource, Carlsbad, Calif.), BCL-2, HIF-1α (BD, Franklin Lakes, N.J.), 4EBP1, FKHR ser256, eIF4E, eIF4E ser209, eIF4G, eIF4G ser1108, IGFR-β, IRS-1, IRS-2, IRS-1 ser612, SGK, Bak, Bax, BAD, BAD ser112, BAD ser136, BAD ser155, B-Raf, mTOR, mTOR ser2448, p70S6 Thr389, p70S6 kinase, p70S6 ser371, S6 kinase ser240/244, Akt, Akt ser473, Akt Thr308, 4EBP1 ser65, 4EBP1 ser70, and 4EBP1 Thr37/46 (Cell Signaling Technology, Danvers, Mass.). The negative control slide was incubated with antibody diluent. Secondary antibody was goat anti-rabbit IgG H+L (1:5000) (Vector Labs, Burlingame, Calif.).

4. Bioinformatics method for microarray analysis. Each array was scanned, spot intensity analyzed, data normalized, and a standardized, single data value was generated for each sample on the array (Image Quant v5.2, GE Healthcare, Piscataway, N.J.). Spot intensity was integrated over a fixed area. Local area background intensity was calculated for each spot with the unprinted adjacent slide background. This resulted in a single data point for each sample, for comparison to every other spot on the array. The Ward method for two-way hierarchical clustering was performed using JMP v5.0 (SAS Institute, Cary N.C.). Wilcoxon two-sample rank sum test was used to compare values between two groups. P values less than 0.05 were considered significant. When we couldn't assume a normal distribution of the variables we used non-parametric methods. We used Kaplan-Meier (log-rank) survival estimates for univariate survival analysis.

5. In vivo xenograft tumor model. Animal studies were performed in accordance with guidelines of the National Institutes of Health Animal Care and Use Committee. Female 4-6 week old beige-SCID mice were purchased from Charles River Laboratories (Wilmington, Mass.). Two million viable cells harvested from mid confluent cultures of either Rh30 alveolar or RD embryonal cells in 0.2 ml diluent (5% Tween-80, 5% polyethylene glycol-400 (Sigma, St. Louis, Mo.)) were injected orthotopically into the gastrocnemius muscle in the left hind leg, and after 1 week mice were randomly assigned to control (n=8) or CCI-779 treatment groups (n=8). Mice were treated IP every 3 days for 30 consecutive days with 20 mg/kg/IP of CCI-779 (Developmental Therapeutics Program, National Cancer Institute and Wyeth, Madison, N.J.) or vehicle alone. Tumor growth was measured every 3 days with calipers, and tumor volume was calculated by the formula V (mm$^3$)=a×b$^2$, where a is the longest tumor axis, and b is the shortest tumor axis. All mice were sacrificed by asphyxiation with $CO_2$ and underwent necropsy for confirmation of tumor growth. Tumors were excised and snap frozen at −80° C. until analysis.

C. Identification of Useful Members of the mTOR Pathway

A study set of tumors from 34 patients was used to identify members of the mTOR pathway as able to discriminate the set of 34 specimens with nearly perfect accuracy. To validate these findings a separate blinded set of tumors from 26 patients, which varied by outcome and response to therapy, was analyzed by reverse phase protein microarray technology, which analyzed multiple signaling events at once. Specific proteins that were able to segregate patients based on outcome in the first set also were able to segregate the second independent set, and are shown in Table 3 below:

TABLE 3

Statistical data for individual protein endpoints from reverse phase protein microarrays for non-metastatic stage 3 Rhabdomyosarcoma samples (n = 26).
Non-metastatic Stage 3 Rhabdomyosarcoma Samples
n = 26, df = 1

| Protein Endpoint | Endpoint Type | One Way Analysis by Outcome (Overall Survival) | | Kaplan-Meier Survival Analysis | |
|---|---|---|---|---|---|
| | | Chi Square | Probability> Chi Square | Chi Square FFS | Chi Square OAS |
| 4EBP1 | Total | 2.0864 | 0.1486 | 0.5080 | 0.7319 |
| 4EBP1 Thr 37/46 | Phospho | 4.4568 | 0.0348 | 0.0106 | 0.0110 |
| 4EBP1Thr37/46:4EBP1 | Ratio | 1.6327 | 0.2013 | 0.9603 | 0.7887 |
| 4EBP1 ser65 | Phospho | 1.7778 | 0.1824 | 0.0785 | 0.1590 |
| 4EBP1 ser65:4EBP1 | Ratio | 0.3735 | 0.5411 | ND | ND |
| 4EBP1 Thr70 | Phospho | 3.1538 | 0.0758 | 0.6454 | 0.9806 |
| 4EBP1 Thr70:4EBP1 | Ratio | 0.0031 | 0.9557 | ND | ND |
| eIF4E | Total | 2.7778 | 0.0956 | 0.0086 | 0.0070 |
| eIF4E ser209 | Phospho | 2.5361 | 0.1113 | 0.6033 | 0.2294 |
| eIF4E ser209:eIF4E | Ratio | 1.6383 | 0.2006 | 0.4556 | 0.2224 |
| mTOR | Total | 2.94 | 0.0864 | 0.2023 | 0.0568 |
| mTOR ser2448 | Phospho | 1.5 | 0.2207 | 0.0079 | 0.0037 |
| mTOR ser2448:mTOR | Ratio | 0.0337 | 0.8542 | 0.5545 | 0.4884 |
| p70S6 | Total | 3.1538 | 0.0758 | 0.8363 | 0.6118 |
| p70S6 Thr389 | Phospho | 4.335 | 0.0373 | 0.0296 | 0.0085 |
| p70S6 Thr389:p70S6 | Ratio | 0.0167 | 0.8973 | 0.3809 | 0.3862 |
| p70S6 ser371 | Phospho | 2.535 | 0.1113 | ND | ND |
| p70S6 ser371:p70S6 | Ratio | 0 | 1.0000 | ND | ND |
| GSK3β | Total | 4.0000 | 0.0455 | 0.0827 | 0.0496 |
| GSK3α/β Tyr279/216 | Phospho | 4.4568 | 0.0348 | 0.0827 | 0.0496 |
| GSK3α/βTyr279/216: GSK3β | Ratio | 3.1605 | 0.0754 | 0.2120 | 0.0629 |
| Akt | Total | 4.0000 | 0.0455 | 0.0316 | 0.0212 |
| Akt ser473 | Phospho | 5.1883 | 0.0227 | 0.0009 | 0.001 |
| Akt ser473:Akt | Ratio | 2.4198 | 0.1198 | 0.3845 | 0.1774 |
| Akt Thr308 | Phospho | 2.0864 | 0.1486 | 0.1459 | 0.0773 |
| Akt Thr308:Akt | Ratio | 0.0494 | 0.8241 | ND | ND |
| eIF4G | Total | 0.3059 | 0.5802 | 0.0155 | 0.0711 |
| eIF4G ser1108 | Phospho | 5.4444 | 0.0196 | 0.0072 | 0.0017 |
| eIF4G ser1108:eIF4G | Ratio | 0.5400 | 0.4624 | 0.9942 | 0.9403 |
| S6 ser240/244 | Phospho | 1.1166 | 0.2907 | 0.0171 | 0.0144 |
| Bak | Total | 4.5938 | 0.0321 | 0.2763 | 0.0771 |
| Bax | Total | 2.3438 | 0.1258 | ND | ND |
| SGK | Total | 1.3538 | 0.2446 | ND | ND |
| BCL-2 | Total | 3.3611 | 0.0668 | ND | ND |
| BAD | Total | 3.2613 | 0.0709 | 0.0103 | 0.0525 |
| BAD ser112 | Phospho | 0.8438 | 0.3583 | 0.6013 | 0.3275 |
| BAD ser112:BAD | Ratio | 0.0338 | 0.8541 | 0.4356 | 0.1696 |
| BAD ser136 | Phospho | 0.0037 | 0.9512 | 0.7995 | 0.7251 |
| BAD ser136:BAD | Ratio | 0.0338 | 0.8541 | ND | ND |

TABLE 3-continued

Statistical data for individual protein endpoints from reverse phase protein microarrays for non-metastatic stage 3 Rhabdomyosarcoma samples (n = 26).

Non-metastatic Stage 3 Rhabdomyosarcoma Samples
n = 26, df = 1

| Protein Endpoint | Endpoint Type | One Way Analysis by Outcome (Overall Survival) | | Kaplan-Meier Survival Analysis | |
|---|---|---|---|---|---|
| | | Chi Square | Probability> Chi Square | Chi Square FFS | Chi Square OAS |
| BAD ser155 | Phospho | 3.375 | 0.0662 | 0.5808 | 0.1999 |
| BAD ser155:BAD | Ratio | 0.0600 | 0.8065 | ND | ND |
| B-Raf | Total | 0.135 | 0.7133 | 0.6458 | 0.2437 |
| FKHR ser256 | Phospho | 1.7778 | 0.1824 | 0.1839 | 0.0113 |
| IRS-1 | Total | 4.8640 | 0.0274 | 0.0015 | 0.0202 |
| IRS-1 ser612 | Phospho | 2.7338 | 0.0982 | 0.3225 | 0.0991 |
| IRS-1 ser612:IRS-1 | Ratio | 0.3564 | 0.5505 | 0.2950 | 0.5065 |
| IRS-2 | Total | 5.6049 | 0.0179 | 0.0544 | 0.1843 |
| IRS-1 ser612:IRS-2 | Ratio | 0.0858 | 0.7696 | 0.5402 | 0.7813 |
| IGFR-β | Total | 4.1572 | 0.0415 | 0.0302 | 0.0917 |
| IRS-1 ser612:IGFR-β | Ratio | 0.2173 | 0.6411 | 0.0578 | 0.1192 |

The top performing predictors, all belong to the mTOR pathway.

D. Exploratory Data Analysis of RMS Tumor Set 1A

Enrichment of tumor cells by Laser Capture Microdissection (LCM) was performed prior to analysis to ensure that the cells for analysis came from within the cancer cell population, without contamination by non-cancer cells (Petricoin et al. (2005), supra; Emmert-Buck et al. (1996) Science 274, 998-1001). For study set 1A (n=33), fifteen specific signaling proteins (FIG. 2A) were initially chosen for reverse phase protein microarray analysis. Unsupervised hierarchical clustering analysis of the 15 protein endpoints revealed two major classes of tumors: one cluster with Akt/mTOR activation/phosphorylation and the other with a comparatively low level of signaling (FIG. 2A). After clinical outcome data was obtained from the COG, these two clusters were compared by Fisher's exact test based on patient characteristics of age, sex, primary site, histology, invasion and lymph node involvement (FIG. 2B). While none of the characteristics reached p<0.05 statistical significance, patients with parameningeal (PM) head and neck primary site tumors comprised 62% of cluster 1, whereas cluster 2 had 27% of patients with PM primary site tumors (Fisher's exact test p=0.06). Additionally, cluster 2 contained 73% alveolar tumors, whereas cluster 1 had 62% embryonal tumors (Fisher's exact test p=0.06). Typically patients with embryonal RMS tumors from orbital or non-parameningeal sites have the best prognosis. These two clusters were not statistically different for commonly accepted prognostic/clinical factors associated with RMS.

We proceeded to correlate the protein analyte values with disease free and overall survival clinical outcome data provided by the COG for study set 1A. A clear partitioning of the tumors emerged after clinical outcome data was obtained from the COG. A decision tree analysis of three proteins—4EBP1, phosphorylated 4EBP1 Thr37/46 and eIF4E—all components of the Akt/mTOR pathway, partitioned patients who were in continuous complete remission from those who recurred and died after being treated with standard therapy. Among these endpoints 4EBP1 and 4EBP1 Thr37/46 individually were found to be significantly correlated with survival by Wilcoxon one-way analysis, 4EBP1 (p<0.0064) and 4EBP1 (p<0.0135) (FIG. 3A). A log rank univariate survival analysis (Kaplan-Meier) supported the association of 4EBP1 with outcome in overall and recurrence free survival in study set 1A (FIG. 3B) (OAS p=0.018, RFS p=0.0370).

For recurrence-free survival in study set 1A, 4EBP1 level ($P_2$=0.0074; HR=7.44; CI: 1.71-32.36) emerged as significant prognostic factor. Thus, for study set 1A (FIG. 1-3) individual components within the Akt/mTOR pathway appeared to correlate with survival.

E. Disease Free and Overall Survival in Rhabdomyosarcoma Patients is Associated with Phosphorylated Components of the Akt and mTOR Pathways.

Based on the findings of study set 1A, an independent set of samples (set 1B, FIG. 1A) were obtained from COG (n=26) for analysis of an expanded set of proteins associated with the Akt/mTOR pathway. Univariate log rank analysis of the two heterogeneous sample sets (set 1A and 1B) revealed no significant difference in overall or recurrence free survival by sample set (OAS p=0.2111, RFS p=0.5824) or histology (OAS p=0.4103, RFS p=0.4312) (FIGS. 1B and C). We analyzed set 1B by LCM and reverse phase protein microarray as in set 1A. We expanded the number of endpoints to 27 to include additional signaling proteins upstream and downstream of Akt and mTOR for an independent evaluation of pathway activation.

Following unblinding of the data, the results for study set 1B (FIG. 4) demonstrated a significant association of disease-free and overall survival with phosphorylated components of the Akt-mTOR pathway. High levels of Akt Ser473, 4EBP1 Thr37/46, eIF4G Ser1108 and p70S6 Thr389 were all significantly associated with poor overall and poor disease-free survival (Akt Ser473 (OAS p<0.001, RFS p<0.0009), 4EBP1 Thr37/46 (OAS p<0.0110, RFS p<0.0106), eIF4G Ser1108 (OAS p<0.0017, RFS p<0.0072), and p70S6 Thr389 (OAS p<0.0085, RFS p<0.0296) (FIG. 4A-D). Each of the 27 components was also evaluated individually for statistical correlation with survivor vs. non-survivor status. Six endpoints—again, all components of the Akt/mTOR network (4EBP1 Thr37, Akt Ser473, eIF4G Ser1108, p70S6 Thr389, Bak and GSK3α/β Tyr279/216)—correlated independently with survival (Wilcoxon one-way analysis 4EBP1 Thr37/46 (p<0.0348), GSK3α/β Tyr279/216 (P<0.0348), eIF4G Ser1108 (p<0.0196), Akt Ser473 (p<0.0227), Bak (p<0.0321), and p70S6 Thr389 (p<0.0373)) (FIG. 4E).

F. IRS-1/Akt/mTOR Feedback Loop is Dysregulated in Non-Survivor Cohort

While tyrosine phosphorylated Insulin Receptor Substrate-1 (IRS-1) activates Akt/mTOR signaling through PI3K, serine phosphorylation of IRS-1, at serine612, by mTOR and p70S6 down regulates IRS-1 tyrosine activation. Thus, IRS-1 is subject to negative feedback regulation in response to Akt/mTOR activation (FIG. 5A). We examined levels of phosphorylated members of the IRS-1/Akt/mTOR feedback loop by reverse phase protein microarray for the tumors in study set 1B (n=26). While levels of IRS-1 Ser612 were no different between the survivors and non-survivors, phosphorylation of IRS-1 Ser612 correlated strongly with phosphorylation of mTOR at Ser2448 in the survivor cohort (Spearman's Rho non-parametric p<0.0027), suggesting a linkage between these two signaling events (FIG. 5B). By contrast, the phosphorylation of these same two signaling proteins was not correlated in the non-survivor cohort (Spearman's Rho non-parametric p=0.7358) (FIG. 5B-C). This lack of correlation with IRS-1 Ser612 phosphorylation also prevailed for the mTOR downstream components eIF4E Ser209 (survivor p=0.0006, non-survivor p=0.1017) and p70S6 Thr389 (survivor p=0.00004, non-survivor p=0.1827) (FIGS. 5B and D). Thus, the negative feedback regulation of IRS-1 activity by the mTOR pathway proteins may be disconnected in the tumors of patients with poor survival. By contrast, IRS-1 signaling appears to exhibit intact negative feedback regulation in the tumors of patients who have long-term survival (FIG. 5A-D).

G. Interrogation of the Phosphorylated Versus Non-Phosphorylated State of Proteins Phosphorylation is an important post-translational modification that has potential significance as a read-out for the activation state of pathways and kinase inhibitor targets. To further investigate potential significant cell signaling proteins within the IRS-1/Akt/mTOR pathway, we extended our analysis to include the following additional endpoints: BAD, eIF4G, IRS-1, IRS-2, IGFR-β, and S6 ser240/244. We conducted Wilcoxon on-way analysis and Kaplan-Meier survival analysis for the phosphorylated protein, the total protein form, and the ratio of the phosphorylated to total forms of key protein endpoints (FIG. 5B). The results clearly demonstrate that the specific phosphorylated forms of the protein endpoints within the Akt-mTOR and associated pathways are associated with survival (p<0.05) compared to the non-phosphorylated total form of the analyte protein (4EBP1 Thr37/46 p<0.03, p70S6 Thr389 p<0.0373, GSK3αβ Y279/216 p<0.348, Akt ser473 p<0.0227, eIF4G ser1108 p<0.0196). This is an important distinction because it is likely that the population of the total protein in a signal pathway node is in excess compared to the phosphorylated form. The phosphorylated form constitutes a subpopulation of the total protein that is actively engaged in signaling.

H. Suppression of the mTOR Pathway in a Mouse Xenograft Model Reduces Tumor Growth.

In order to validate the functional significance of our IRS-1/Akt/mTOR network analysis we employed rapamycin analogs, which are well-characterized inhibitors of the mTOR protein kinase pathway, using a mouse xenograft treatment model. Either RD embryonal cells or Rh30 alveolar cells were injected orthotopically into the hind leg of beige SCID mice. These two different cell-lines were used to determine the effects of mTOR inhibition in different histological tumor categories. The rapamycin analog CCI-779 (Wyeth, Madison, N.J.) dosage was 20 mg/kg, which corresponds to dosages currently administered to humans in phase I and II clinical trials (Raymond et al. (2004), *J Clin Oncol* 22, 2336-2347; Smolewski et al. (2006) *Anticancer Drugs* 17, 487-494). Administration of CCI-779 at doses that were verified to suppress the phosphorylation of mTOR downstream targets, profoundly reduced the growth of rhabdomyosarcoma xenografts as measured in the SCID-beige murine model (Rh30 xenograft group p=0.0002; RD xenograft group p=0.00008, n=8 for both groups) (FIG. 6A-C). Suppression of the mTOR pathway was monitored by measuring the phosphorylation of 4EBP1 and S6 ribosomal protein, which are well-established downstream targets of mTOR. CCI-779 inhibited the phosphorylation of these downstream targets commensurate with a blockade in mTOR signaling in both the Rh30 alveolar and RD embryonal xenograft derived tumors.

I. Discussion

In this Example, analysis of protein signaling pathways was conducted blinded to treatment or survival utilizing two independent RMS tumor study sets for which twelve-year follow-up data was available. The patients were subsequently treated on the recently completed IRS IV study, the COG D9502, or the on-going COG D9803 studies. Two independent study sets (FIG. 1A, Table 1A and 1B) were procured randomly from the pool of frozen specimens. Each study set represented a variety of treatment modalities, histological subtypes, and tumor sites. The two sets differed in the proportion of samples with alveolar versus embryonal histology (FIG. 1) (3, 4). Although the sample sets were heterogeneous, there was no statistically significant difference in either overall survival or recurrence free survival between the two sample sets (overall survival p=0.2111, recurrence free survival p=0.5824) (FIG. 1B).

Current prognostic indicators for patients diagnosed with Rhabdomyosarcoma are: age, stage, group, histology, and primary site, with patients in the 1-8 year age group with embryonal RMS from orbital or non-parameningeal head and neck sites having the best prognosis (15). Using unsupervised clustering analysis, we sought to determine if any protein signaling signature correlated with histological subtype. For the first study set, fifteen specific signaling proteins (FIGS. 2A and 3A) were initially chosen because they constituted a broad survey of multiple pro-survival related events. A multiplexed measurement of the chosen phosphorylation states provided an averaged portrait of the ongoing kinase activity events within selected networks that drive cellular growth or survival.

The initial unsupervised clustering analysis was not significantly associated with histology but there was clear portioning of the samples into two clusters, with one cluster exhibiting activation of Akt/mTOR proteins (FIG. 2A). Therefore, clinical outcome data was obtained from the COG for further exploratory associations between the protein endpoints and clinical data. The results of set 1A revealed a statistically significant association between survival and the activation/suppression of proteins linked to the Akt/mTOR (mammalian target of rapamycin) signaling pathway (FIG. 3A).

Based on the results of set 1A we expanded this exploratory analysis to 27 endpoints applied to a second independent set of samples (FIG. 1A, Table 1B). Proteins that appeared to correlate with survival or failure in the second study set were linked together in the Akt/mTOR kinase pathway (13, 27, 28). Phosphorylated components of IRS-1 (insulin receptor substrate), Akt, mTOR, 4EBP1 (elongation binding factor), GSK3α/β (glycogen synthase kinase-3), and p70S6 were found to be associated with outcome (FIG. 4). IRS-1, Akt and GSK3β are associated with cell growth, survival, insulin response and glucose metabolism. mTOR, 4EBP1 and p70S6 are essential components of protein translation, in which phosphorylation of 4EBP1 releases 4EBP1 from eIF4E, activating cap-dependent translation. These pathways are known to be involved in the regulation of prosurvival and translation for a group of proteins that are important for cell cycle and apoptosis, including several known oncogenes such as cyclin D, c-myc, and Hif-1alpha.

Akt/PKB (protein kinase B) plays a central role in multiple cellular functions including glycogen synthesis, cell cycle regulation and maintenance of cell survival and apoptosis. Although Akt Ser473 correlated with survival ($p<0.02$) for study set 1B, it did not correlate with survival in set 1A ($p=0.2460$). This may have been due to differences in the relative composition of tumor histologies and sites of origin between the two groups (FIG. 1A).

A variety of autocrine and paracrine stimuli including hormones, growth factors, mitogens, cytokines and G-protein-coupled receptor agonists elicit 4EBP1 hyperphosphorylation and concomitant loss of eIF4E-binding activity in the mTOR pathway. Activation of phosphoinositide 3 kinase (PI3K) or the downstream effector kinase Akt leads to 4EBP1 hyperphosphorylation, affecting its release from eIF4E. Phosphorylation of 4EBP1 on multiple loci is associated with linkage to the Insulin receptor pathway and the PI3K pathway. Six phosphorylation sites have been identified on 4EBP1. Thr37, Thr46, Ser65, and Thr70 become phosphorylated after insulin stimulation, and such phosphorylation can be blocked by rapamycin (inhibitor of mTOR) and wortmannin (inhibitor of PI3K). It has been shown that mTOR itself, as well as an mTOR associated kinase, directly phosphorylates sites on 4EBP1. Gingras et al established that phosphate groups are first added to Thr 37 and Thr 46. This priming phosphorylation is required for the phosphorylation of other sites necessary for binding. Thus, multiple phosphorylation events triggered from multiple kinases, primed by Thr 37/46, are involved in the release of 4E-BP1 from eIF4E.

Tyrosine phosphorylated Insulin Receptor Substrate-1 (IRS-1) activates Akt/mTOR signaling through PI3K, serine phosphorylation of IRS-1 (at serine612) by mTOR and p70S6 down regulates IRS-1 tyrosine activation. Thus, it has been suggested that IRS-1 is subject to negative feedback regulation in response to Akt/mTOR activation through p70S6 (FIG. 5A). We examined the IRS-1 feedback loop interrelationship with components of the Akt and mTOR pathway by non-parametric correlations (FIG. 5B-D). Interrogation of IRS-1 serine612 and various potential interacting proteins provided a means to assess the protein interactions with the actual phosphorylation site involved in the negative feedback regulation of IRS-1. The average level of IRS-1ser 612 was not statistically different between tumors from patients with favorable outcome compared to those with poor outcome (FIG. 4E), suggesting that the level of IRS-1 upstream activity was similar. While the average level of IRS-1 phosphorylation was similar in the favorable versus poor outcome cases, the correlation of individual IRS-1 phosphorylation levels in each tumor with phosphorylation levels of Akt and mTOR pathway proteins was highly dissimilar in these two phenotypes. On the other hand Bax, FKHR ser256, and 4EBP1 Thr70 were significantly correlated for both groups (FIG. 5B). As shown in FIG. 5, there was a strong positive correlation ($p=0.00269$) of IRS-1 ser612 with mTOR ser2448 and with p70S6 Thr289 ($p=0.00004$) in tumors with favorable outcome (FIG. 5B-D). This suggests a linkage consistent with a feed back loop between mTOR and IRS-1 and the likelihood that it could exist in the in vivo state in these tumors with favorable outcomes. These data support a selective disconnection of the feedback loop in tumors with poor outcome.

The implications of these differences in the IRS-Akt-mTOR interconnectivity of survivors and non-survivors are two-fold. Firstly, the apparent lack of interconnection between IRS-1 and mTOR could disrupt the normal negative feedback regulation. This could result in increased phosphorylation of Akt as we noted in the tumors from patients with poor outcomes and illustrated in FIG. 5A. Secondly, mTOR inhibitor therapy for aggressive tumors, in which the negative feed back loop is not functioning, would fail to cause the increased phosphorylation of Akt. Baseline levels of phosphorylated Akt and MTOR may be elevated in aggressive tumors in which the negative feedback regulation of mTOR through IRS-1 is disrupted, leading to the sustained growth and survival of the tumor.

The identified 4E-BP1 phosphorylation sites are known to be specifically inhibited by rapamycin treatment. In order to validate the functional significance of our network analysis revealing mTOR pathway suppression observed in patients who had a favorable treatment outcome, we exploited the existence of rapamycin analogs, which are well-characterized inhibitors of the mTOR protein kinase pathway. Some of these analogs are currently in phase I and II clinical trials of adults with cancer (Raymond et al. (2004), supra; Smolewski et al. (2006) supra). Suppression of the mTOR pathway was monitored by measuring the state of phosphorylation of 4EBP1 and S6 kinase, which are well-established downstream substrates of mTOR (13, 27, 28, 30, 31). CCI-779 inhibited the expected phosphorylation of the downstream targets commensurate with a blockade in mTOR signaling in xenograft tumors derived from Rh30 alveolar or RD embryonal cells (FIG. 6).

In summary, protein pathway analysis of microdissected human RMS clinical specimens, procured prior to treatment, revealed a strong association between activation of the Akt/mTOR pathway and a poor outcome in this initial, exploratory analysis. This observation was found to be consistent between two independently analyzed clinical study sets. Moreover, the functional significance of IRS-1/Akt/mTOR pathway activation in RMS was verified using the specific targeted inhibitor CCI-779 to suppress tumor growth in a SCID-beige RMS xenograft model. These data support the rationale for using rapamycin analogs in this tumor type as a potential way to modulate poor prognosis patients into more durable outcomes. Combination therapy strategies can be aimed at blocking both upstream signaling factor activation, as well as downstream mTOR signaling, as a means of augmenting standard cytotoxic RMS therapy.

Example II

Lung Cancer Phosphoproteomic Analysis Using Reverse Phase Protein Microarays; the Importance of the mTOR Pathway in Determining Outcome in Non-Small Cell Lung Cancer, the Most Common Form of Lung Cancer A. Materials and Methods 1. Samples. Twenty early-stage lung adenocarcinoma surgical specimens. Lung surgical resections were collected from patients and frozen at the time of surgery. (Patient survival was confirmed by the National Death Index)

2. Frozen sections. 8 µm frozen tissue sections were prepared on silanized slides.

3. Laser Capture Microdissection (LCM). Pure tumor cell populations were procured using Molecular Devices' PixCell or Veritas instruments.

4. Reverse phase protein microarrays were printed with on Whatman Schleicher and Schuell FAST slides using Affymetrix GMS 417 pin and ring style arrayer (samples were printed in duplicates, at 10 hits per dot).

5. Immunostaining. Microarrays were probed for specific proteins on a Dako Autostainer using Dako's catalyzed signal amplification chemistry (horseradish peroxidase mediated deposition of biotinyl tyramide) with chromogenic detection (DAB).

B. Partition Analysis

Microarray spot intensity was performed with Image Quant ver5.2.

Figure 7A:
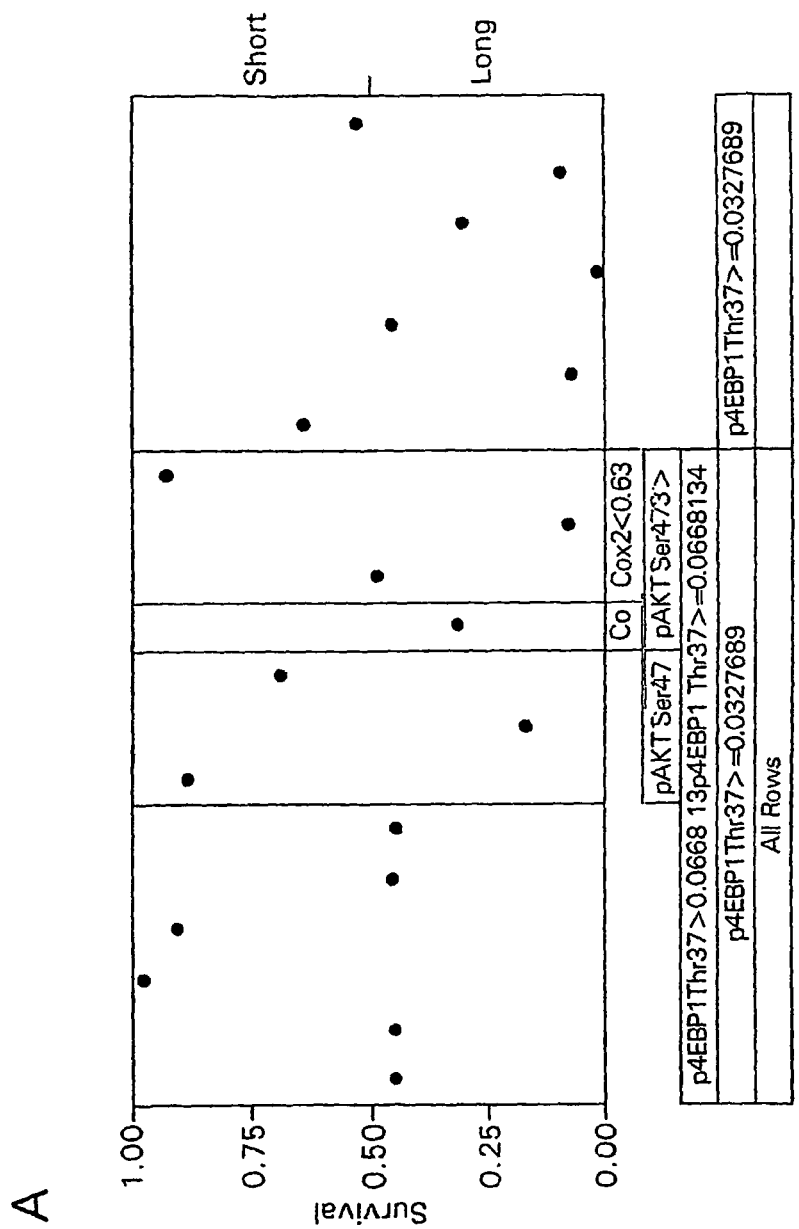
FIG. 7 shows Partition Analysis of lung adenocarcinoma tumor samples.
Figure 7B:
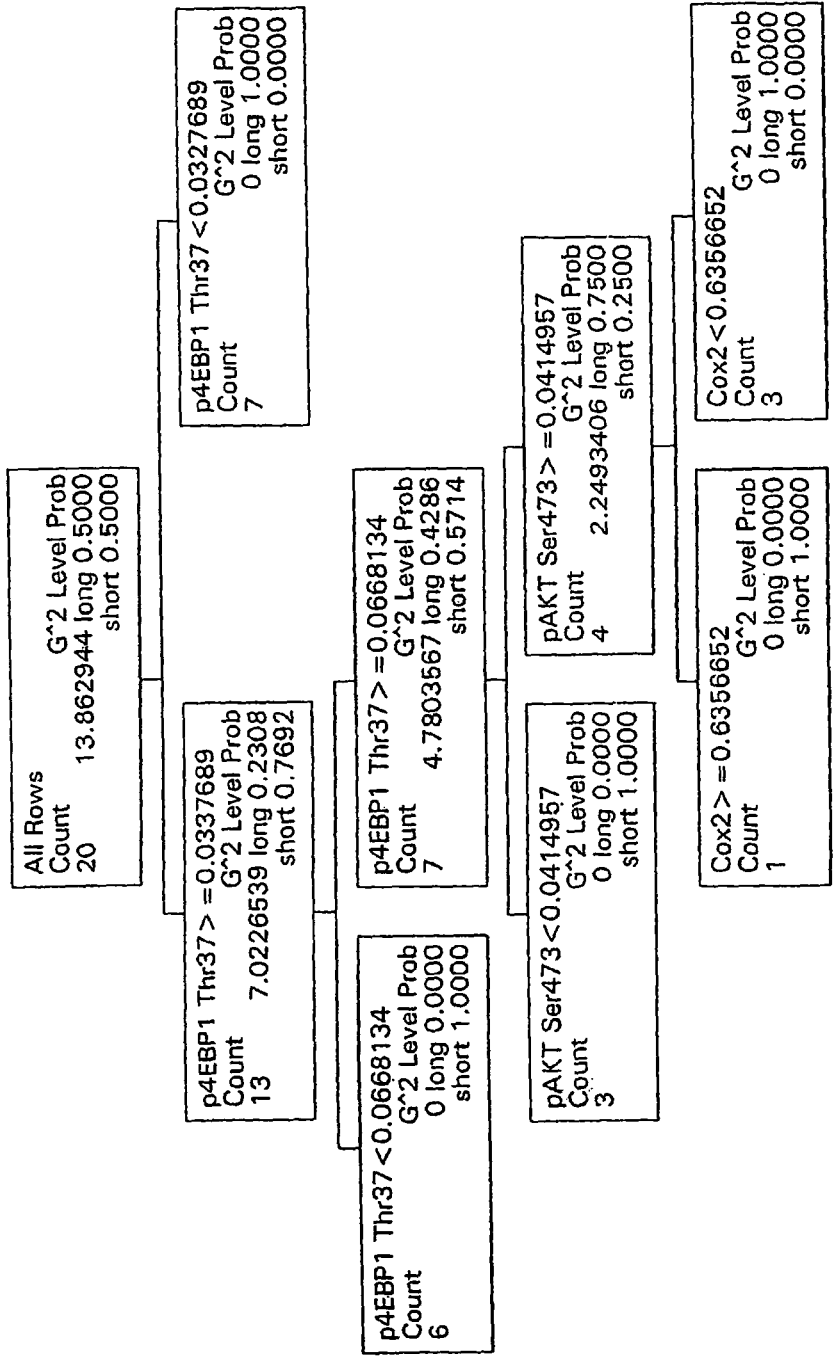

JMP software was used for Two-way Hierarchical Clustering (Ward method) and partition analysis. The results are shown in Table 4 below and in FIG. 7.

TABLE 4

Antibody probes used for immunostaining the reverse phase protein microarray.

| Antibody | Vendor | Dilution |
|---|---|---|
| AKT (ser 473) | Cell Signaling | 1:100 |
| AKT (thr 308) | Cell Signaling | 1:100 |
| ERK1/2 (thr 202/tyr204) | Cell Signaling | 1:2000 |
| BCL2 (ser 70) | Cell Signaling | 1:200 |
| IRS (ser 612) | Cell Signaling | 1:50 |
| EGFR (tyr 1045) | Cell Signaling | 1:100 |
| EGFR (tyr 845) | Cell Signaling | 1:100 |
| EGFR (tyr 992) | Cell Signaling | 1:100 |
| EGFR (tyr 1148) | BioSource | 1:200 |
| EGFR (tyr 1068) | Cell Signaling | 1:100 |
| EGFR (tyr 1173) | BioSource | 1:100 |
| Her2 (tyr1248) | Cell Signaling | 1:100 |
| 14-3-3 zeta, gamma, eta | Upstate | 1:20,000 |
| Cox2 | Upstate | 1:500 |
| 4EBP1 (thr 37) | Cell Signaling | 1:200 |
| APC2 | Lab Vision | 1:100 |
| BUB3 | BD Transduction | 1:250 |
| Cyclin D1 | BD Transduction | 1:200 |
| Cyclin E | BD Transduction | 1:100 |
| SMAD2 (ser 465) | Cell Signaling | 1:250 |

C. Analysis by RPMA by Kaplan-Mier Survival Plots

Figure 8:
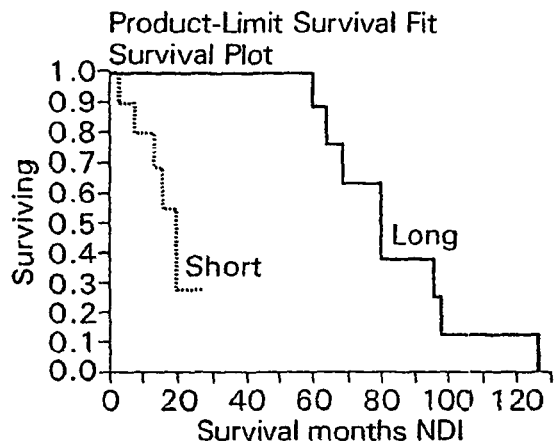
FIG. 8 shows an analyte-link survival fit grouped by p4EBP1 cutpoint, for lung cancer.
Figure 9:
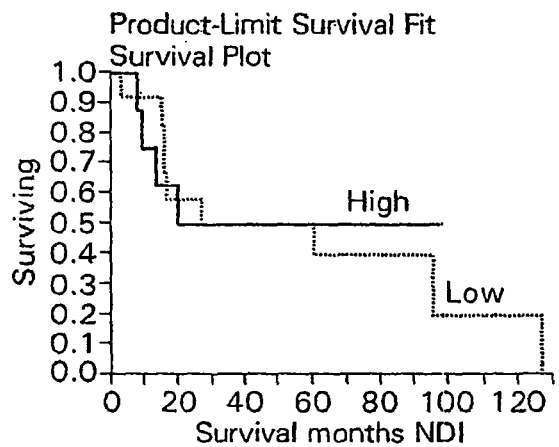
FIG. 9 shows an analyte-link survival fit grouped by p4EBP1 pAKTser473 cutpoint, for lung cancer.

In this set, 10 patients with long term survival and 10 patients with short term survival were analyzed by reverse phase array analysis, and based on principal component analysis. The results, shown as a Kaplan-Mier survival plot (FIGS. 8 and 9), show that once again, components of the AKT/mTOR pathway were found to be the principal drivers of outcome. Again, those patients with elevated p4EBP1 and pAKT had significantly shorter overall survival times.

Example III

Breast Cancer Phosphoproteomic Analysis using Reverse Phase Protein Microarays

In this Example, a study set of tumors taken from ER+ lymph node negative and lymph node positive breast cancer patients, with at least 10 years of follow up and all treated with tamoxifen monotherapy, were analyzed by molecular network analysis using reverse phase protein microarrays. Out of the 55 phosphoendpoints analyzed, the major principal components of outcome segregation belonged to the mTOR pathway. Importantly, the mTOR pathway components, pEBP1 mainly, and p70S6, could segregate outcome regardless of lymph node status.

Figure 10:
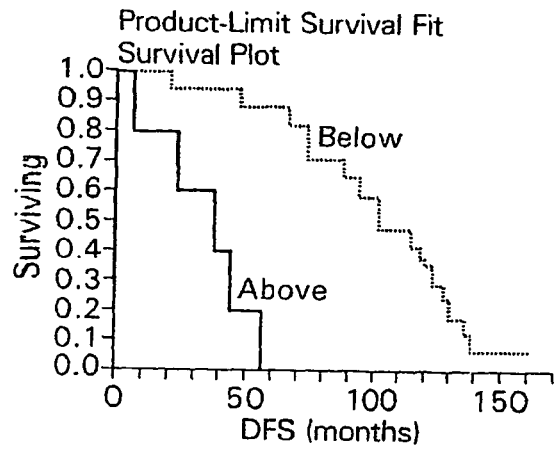
FIG. 10 shows an analyte-link survival fit grouped by p4EB-P1 cutpoint, for breast cancer; survival from LN-only subset
Figure 11A:
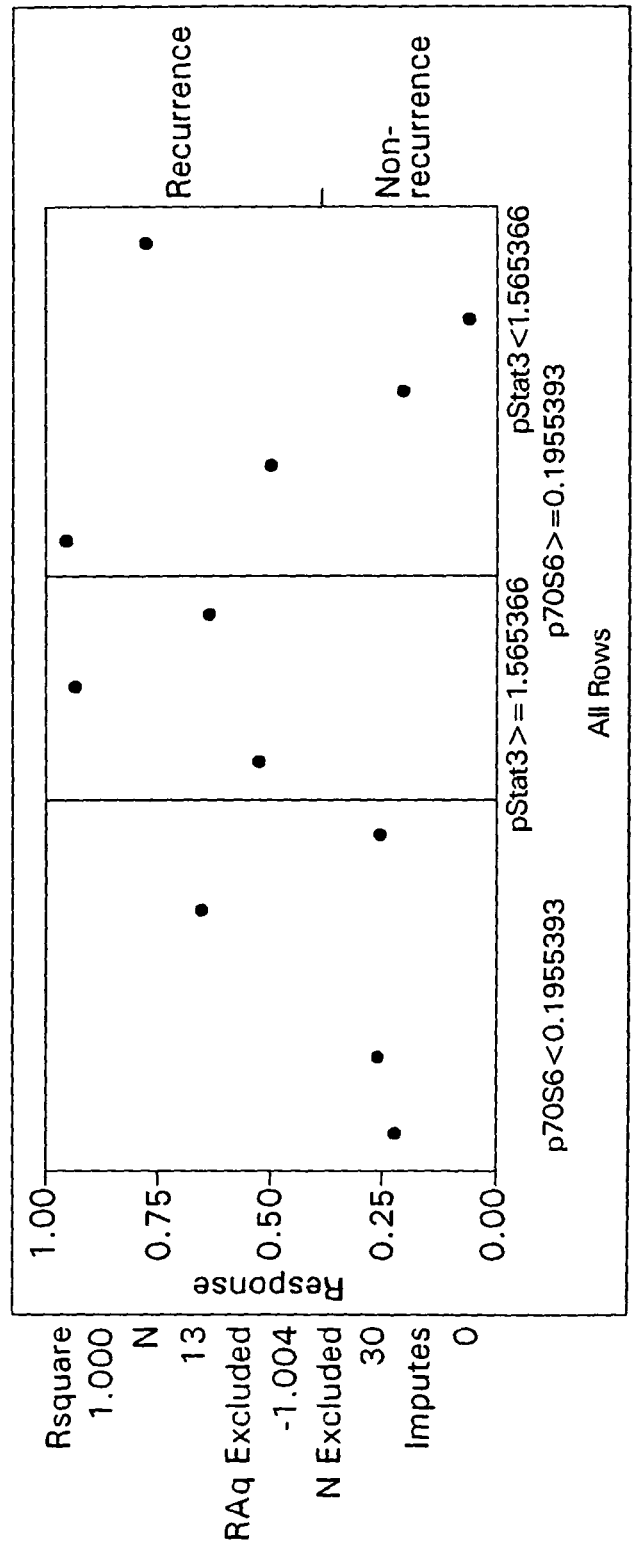
FIG. 11 shows a Partition Analysis of the LN+ populations showing p70S6 as a principal component of segregation, for breast cancer.
Figure 11B:
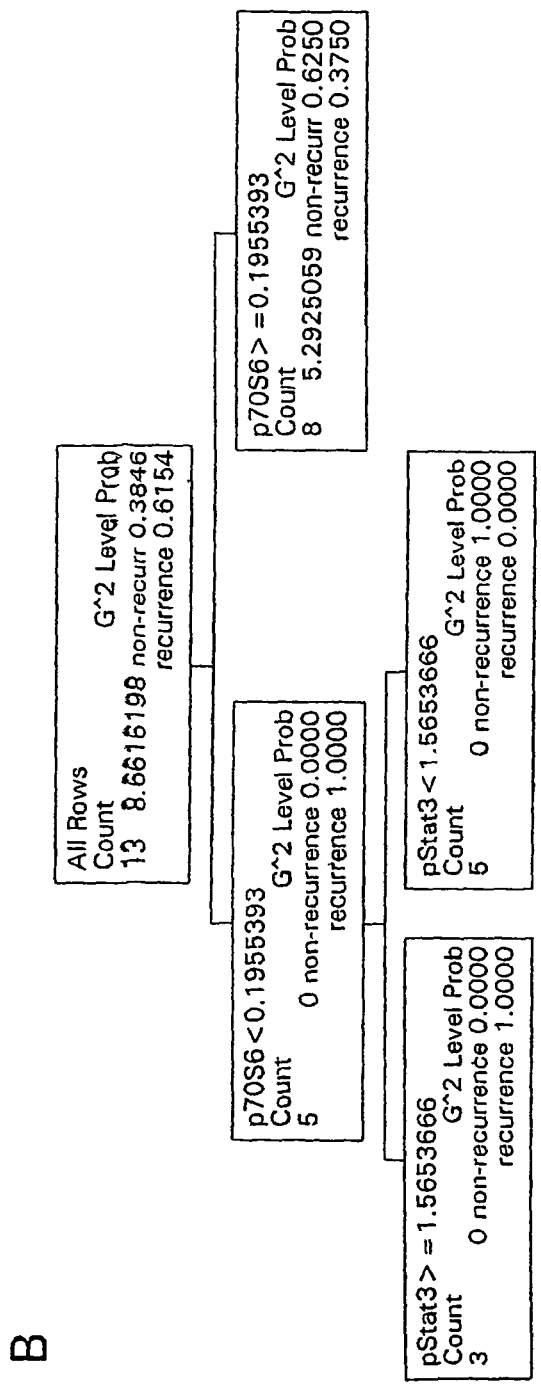
Figure 12:
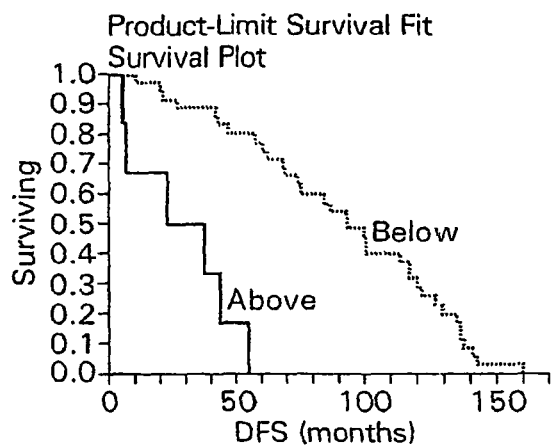
FIG. 12 shows shows a survival plot from all cases, both LN– and LN+, for breast cancer.

FIG. 10 shows a product-link survival fit grouped by p4EBP1; survival from LN-only subset. FIG. 11 shows a Partition Analysis of the LN+ populations showing p70S6 as a aprincipal component of segregation. FIG. 12 shows a survival plot from all cases, both LN− and LN+.

Conclusion: The data clearly support the conclusion that time to recurrence for women with ER+breast cancer, regardless of lymph node status, and treated with tamoxifen monotherapy was strongly associated with the phosphorylation state of specific components of the MTOR pathway. This information can be the basis for the decision to a) decide who should receive tamoxifen therapy and/or b) administer secondary therapy to that subset of patients predicted to have a poor survival. Suitable such secondary therapeutic agents are discussed elsewhere herein.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including U.S. provisional application No. 60/727,510, filed Oct. 18, 2005) cited above and in the figures are hereby incorporated in their entirety by reference.

We claim:

1. A method for predicting the response of a subject with cancer to a conventional chemotherapeutic agent, comprising
measuring the phosphorylation state of at least one member of the mTOR pathway, and/or of at least one member of an interconnected polypeptide pathway, in a cancer tissue or cancer cell sample from the subject, wherein the member of the interconnected polypeptide pathway (i) is from the Akt pathway, (ii) is from the IRS pathway, (iii) is pRb, and/or (iv) is a substrate of Akt,
comparing the measured phosphorylation state to a baseline value to determine whether or not it is elevated, and
concluding, if the phosphorylation state is elevated, that the subject is a non-responder to the conventional chemotherapeutic agent, or
concluding, if the phosphorylation state is not elevated, that the subject is a responder to the conventional chemotherapeutic agent.

2. The method of claim 1, wherein the phosphorylation state that is measured is: (i) of at least one member of the mTOR pathway; or (ii) of at least one member of the Aid pathway; or (iii) of at least one member of the IRS pathway; or (iv) of at least one member of the mTOR pathway and at least one member of the Akt pathway; or (v) of at least one member of the mTOR pathway and at least one member of the IRS pathway; or (vi) of at least one member of the Akt pathway and at least one member of the IRS pathway; or (vii) of at least one member of the mTOR pathway, at least one member of the Akt pathway, and at least one member of the IRS pathway.

3. The method of claim 1, wherein the mTOR and/or interconnected polypeptide pathway member is Akt-kinase, mTOR, 4E-BP1/PHAS-1, p70s6k, eIF-4E, eIF-4G, PTEN, PDK1, GSK3Beta, TSC1/2, ILK, Gab1/2, p27Kip1, FKHR, FKHRL, eNOS, ASK1, BAD, pRAS40, 14-3-3, or CHK1.

4. The method of claim 1, wherein the phosphorylation state of the pathway member is measured using an antibody to the phosphorylation site of at least one member selected from: PI3-kinase, Akt-kinase, mTOR, 4E-BP1/PHAS-1, p70s6k, eIF-4E, eIF-4G, PTEN, PDK1, GSK3Beta, TSC1/2, ILK, Gab1/2, p27Kip1, FKHR, FKHRL, eNOS, ASKI, BAD, pRAS40, 14-3-3, or CHK1.

5. The method of claim 1, wherein the mTOR and/or interconnected polypeptide pathway member is pRb, GSK3, or Bak.

6. The method of claim 1, wherein the cancer is (i) breast cancer, (ii) rhabdomyosarcoma, (iii) lung cancer, (iv) non-small cell lung cancer, or (v) not associated with a loss of function of PTEN and/or a mutated and activated Akt.

7. The method of claim 1, comprising measuring in the sample from the subject the level of the phosphorylation state of IRS (Ser 612) and one or more of:
   a. Akt (Thr 308),
   b. mTOR (Ser 2448),
   c. 4EBP1 (Ser 65 or Thr70), and
   d. p70 S6 (The389 or Ser371), and
   concluding that a subject that exhibits a significantly decreased level of the phosphorylation state of a, b, c, and/or d, compared to the level of the phosphorylation state of IRS (Ser 612), is likely to be responsive to the conventional chemotherapeutic agent, or
   concluding that a subject that exhibits a significantly increased level of the phosphorylation state of a, b, c, and/or d, compared to the level of the phosphorylation state of IRS (Ser 612), is likely not to be responsive to the conventional chemotherapeutic agent.

8. The method of claim 7, further comprising measuring in the sample the level of the phosphorylation state of one or more of the following proteins:
   e. GSK3a/b (Y279/216),
   f. eIF4E (Ser 209),
   g. eIF4G (Ser 1108),
   h. p70S6 (Thr 389),
   i. p70S6 (Ser 371),
   j. BAD (Seri 12),
   k. BAD (Ser136), r
   l. AKT (S473) and
   m. Bcl (Ser 70), and
   concluding that a subject that exhibits a significantly decreased level of the phosphorylation state of one or more of e-m, compared to the level of the phosphorylation state of IRS (Ser 612), is further likely to be responsive to the conventional chemotherapeutic agent, or
   concluding that a subject that exhibits a significantly increased level of the phosphorylation state of one or more of e-m, compared to the level of the phosphorylation state of IRS (Ser 612), is further likely not to be responsive to the conventional chemotherapeutic agent.

9. The method of claim 7, wherein the subject has breast cancer and the conventional chemotherapeutic agent is Tamoxifen.

10. The method of claim 1, wherein the cancer is not associated with a loss of function of PTEN and/or a mutated and activated Akt.

11. The method of claim 1, wherein the phosphorylation states are measured using a reverse phase protein microarray (RPMA).

12. The method of claim 1, wherein the phosphorylation states are measured in cancer cells obtained by laser capture microdissection.

13. The method of claim 1, wherein the mTOR and/or interconnected polypeptide pathway member is p70s6k, 4E-BP1/PHAS-1, mTOR, Akt-kinase, eIF-4E, eIF-4G, GSK3Beta, FKHR, FKHRL, or pRAS40.

14. The method of claim 1, wherein the mTOR and/or interconnected polypeptide pathway member is p70s6k, 4E-BP1/PHAS-1, mTOR, Akt-kinase, eIF-4E, or eIF-4G.

15. A method for predicting the response of a subject with cancer to a conventional chemotherapeutic agent, comprising measuring the phosphorylation state of at least one member of the mTOR pathway in a cancer tissue or cancer cell sample from the subject,
   comparing the measured phosphorylation state to a baseline value to determine whether or not it is elevated, and
   concluding, if the phosphorylation state is elevated, that the subject is a non-responder to the conventional chemotherapeutic agent, or
   concluding, if the phosphorylation state is not elevated, that the subject is a responder to the conventional chemotherapeutic agent.

16. The method of claim 15, wherein the cancer is (i) breast cancer, (ii) rhabdomyosarcoma, (iii) lung cancer, (iv) non-small cell lung cancer, or (v) not associated with a loss of function of PTEN and/or a mutated and activated Akt.

17. The method of claim 15, wherein the subject has breast cancer and the conventional chemotherapeutic agent is Tamoxifen.

18. The method of claim 15, wherein the cancer is not associated with a loss of function of PTEN and/or a mutated and activated Akt.

19. The method of claim 15, wherein the phosphorylation states are measured using a reverse phase protein microarray (RPMA).

20. The method of claim 15, wherein the phosphorylation states are measured in cancer cells obtained by laser capture microdissection.

21. The method of claim 15, wherein the mTOR polypeptide pathway member is p70s6k, 4E-BP1/PHAS-1, mTOR, eIF-4E, or eIF-4G.

22. A method for selecting a treatment for a subject having cancer, comprising
   predicting the subject's response to a conventional chemotherapeutic agent by the method of claim 15 and,
   selecting treatment with a conventional method of chemotherapy, if no significant increase in the level of the phosphorylation state of the member is observed compared to the baseline value, or
   selecting treatment with an inhibitor of the mTOR pathway, if a significantly increased level of the phosphorylation state of the member compared to the baseline value is observed.

23. The method of claim 22, wherein the mTOR polypeptide pathway member is p70s6k, 4E-BP1/PHAS-1, mTOR, eIF-4E, or eIF-4G.

24. A method for selecting a treatment for a subject having cancer, comprising
   predicting the subject's response to a conventional chemotherapeutic agent by the method of claim 1 and,
   selecting treatment with a conventional method of chemotherapy, if no significant increase in the level of the phosphorylation state of the member is observed compared to the baseline value, or
   selecting treatment with an inhibitor of the mTOR pathway or of an interconnected polypeptide pathway, if a significantly increased level of the phosphorylation state of the member compared to the baseline value is observed, wherein the member of the interconnected polypeptide pathway (i) is from the Akt pathway, (ii) is from the IRS pathway, (iii) is pRb, and/or (iv) is a substrate of Akt.

25. The method of claim 24, wherein the phosphorylation state that is measured is: (i) of at least one member of the mTOR pathway; or (ii) of at least one member of the Akt pathway; or (iii) of at least one member of the IRS pathway; or (iv) of at least one member of the mTOR pathway and at least one member of the Akt pathway; or (v) of at least one member of the mTOR pathway and at least one member of the IRS pathway; or (vi) of at least one member of the Akt pathway and at least one member of the IRS pathway; or (vii) of at least one member of the mTOR pathway, at least one member of the Akt pathway, and at least one member of the IRS pathway.

26. The method of claim 24, wherein the mTOR and/or interconnected polypeptide pathway member is Akt-kinase, mTOR, 4E-BP1/PHAS-1, p70s6k, eIF-4E, eIF-4G, PTEN, PDK1, GSK3Beta, TSC1/2, ILK, Gab1/2, p27Kip1, FKHR, FKHRL, eNOS, ASK1, BAD, pRAS40, 14-3-3, or CHK1.

27. The method of claim 15, wherein the mTOR and/or interconnected polypeptide pathway member is p70s6k, 4E-BP1/PHAS-1, mTOR, Akt-kinase, eIF-4E, eIF-4G, GSK3Beta, FKHR, FKHRL, or pRAS40.

28. The method of claim 15, wherein the mTOR and/or interconnected polypeptide pathway member is p70s6k, 4E-BP1/PHAS-1, mTOR, Akt-kinase, eIF-4E, or eIF-4G.

* * * * *

UNITED STATES PATENT AND TRADEMARK OFFICE
CERTIFICATE OF CORRECTION

PATENT NO.        : 8,628,931 B2
APPLICATION NO.   : 12/083866
DATED             : January 14, 2014
INVENTOR(S)       : Liotta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1548 days.

Signed and Sealed this
Twenty-second Day of September, 2015

Michelle K. Lee
*Director of the United States Patent and Trademark Office*